United States Patent
Fritz et al.

(10) Patent No.: US 10,429,386 B2
(45) Date of Patent: Oct. 1, 2019

(54) **ANTIBODIES TO THE SURFACE OF *TOXOPLASMA GONDII* OOCYSTS AND METHODS OF USE THEREOF**

(71) Applicant: The Regents of the University of California, Oakland, CA (US)

(72) Inventors: Heather Fritz, Davis, CA (US); Patricia Conrad, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/548,062

(22) PCT Filed: Mar. 8, 2016

(86) PCT No.: PCT/US2016/021321
§ 371 (c)(1),
(2) Date: Aug. 1, 2017

(87) PCT Pub. No.: WO2016/144933
PCT Pub. Date: Sep. 15, 2016

(65) Prior Publication Data
US 2018/0017557 A1 Jan. 18, 2018

Related U.S. Application Data

(60) Provisional application No. 62/146,063, filed on Apr. 10, 2015, provisional application No. 62/131,098, filed on Mar. 10, 2015.

(51) Int. Cl.
*G01N 33/53* (2006.01)
*G01N 33/569* (2006.01)
*C07K 16/20* (2006.01)

(52) U.S. Cl.
CPC ....... *G01N 33/56905* (2013.01); *C07K 16/20* (2013.01); *C07K 2317/33* (2013.01); *G01N 2333/45* (2013.01); *G01N 2469/10* (2013.01)

(58) Field of Classification Search
CPC .............................................. G01N 33/56905
See application file for complete search history.

(56) References Cited

U.S. PATENT DOCUMENTS 6,777,222 B1 8/2004 Vesey et al.
2008/0196112 A1* 8/2008 Romagne ........... A01K 67/0278
800/4

OTHER PUBLICATIONS

Possenti et al., (2010) "Molecular characterisation of a novel family of cysteine—rich proteins of Toxoplasma gondii and ultrastructural evidence of oocyst wall localisation." International journal for parasitology, 40(14):1639-1649.
Simmons, et al., (2001) "Concentration and Detection of Cryptosporidium Oocysts in Surface Water Samples by Method 1622 Using Ultrafiltration and Capsule Filtration", Applied and Environmental Microbiology. 67(3)1123-1127.
Robert-Gangneux, Florence and Darde, Marie-Laure, (2012) "Epidemiology of and Diagnostic Strategies for Toxoplasmosis", Clinical Microbiology Reviews, 25(2):264-296.
Dumetre, Aurelien and Darde, Marie-Laure, (2005) "Immunomagnetic separation of Toxoplasma gondii oocysts using a monoclonal antibody directed against the oocyst wall", Journal of Microbiological Methods, 61:209-217.
Dumetre, Aurelien and Darde, Marie-Laure, (2003) How to detect Toxoplasma gondii oocysts in environmental samples?, FEMS Microbiology Reviews, 27:651-661.
Buchholz, et al., (2011) "Identification of Tissue Cyst Wall Components by Transcriptome Analysis of In Vivo and In Vitro Toxoplasma gondii Bradyzoites", Eukaryotic Cell, 10(12):1637-1647.
Fritz, et al., (2012) "Proteomic Analysis of Fractionated Toxoplasma Oocysts Reveals Clues to Their Environmental Resistance", PLoS One, 7(1):1-14.
Fritz, et al., (2012) "Transcriptomic Analysis of Toxoplasma Development Reveals Many Novel Functions and Structures Specific to Sporozoites and Oocysts", PLoS One, 7(2):1-18.
Muñoz-Zanzi Claudia A., et al., (2010) "Toxoplasma gondii Oocyst—specific Antibodies and Source of Infection", Emerging Infectious Diseases, 16(10):1591-1593.
Fritz, H, et al., (2012) "Methods to produce and safely work with large numbers of Toxoplasma gondii oocysts and bradyzoite cysts", J Microbiol Methods, 88: 47-52.
Shapiro, Karen, et al., (2009) "Surface Properties of Toxoplasma gondii Oocysts and Surrogate Microspheres", Applied and Environmental Microbiology, 75(4):1185-1191.

* cited by examiner

*Primary Examiner* — Albert M Navarro
(74) *Attorney, Agent, or Firm* — Otto Guedelhoefer; Bozicevic, Field & Francis LLP

(57) ABSTRACT

The present disclosure provides antibodies that bind the surface of *Toxoplasma gondii* oocysts, methods for using such antibodies and kits and devices for practicing such methods. Such antibodies, methods, kits and devices find use in detection of *T. gondii* oocysts and the isolation of such oocysts from samples including environmental samples, food-based samples, diagnostic samples, and the like.

12 Claims, 5 Drawing Sheets
Specification includes a Sequence Listing.

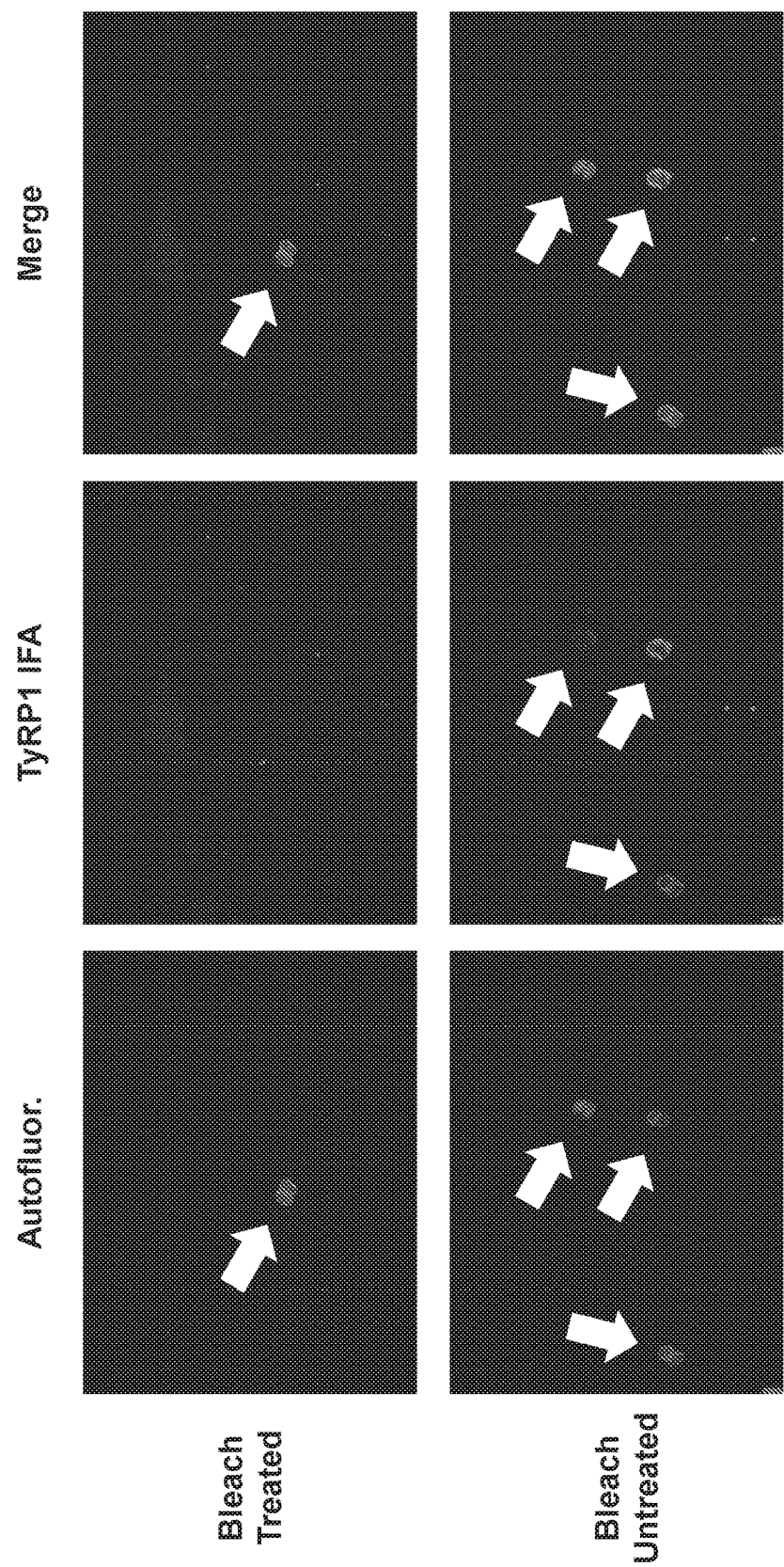

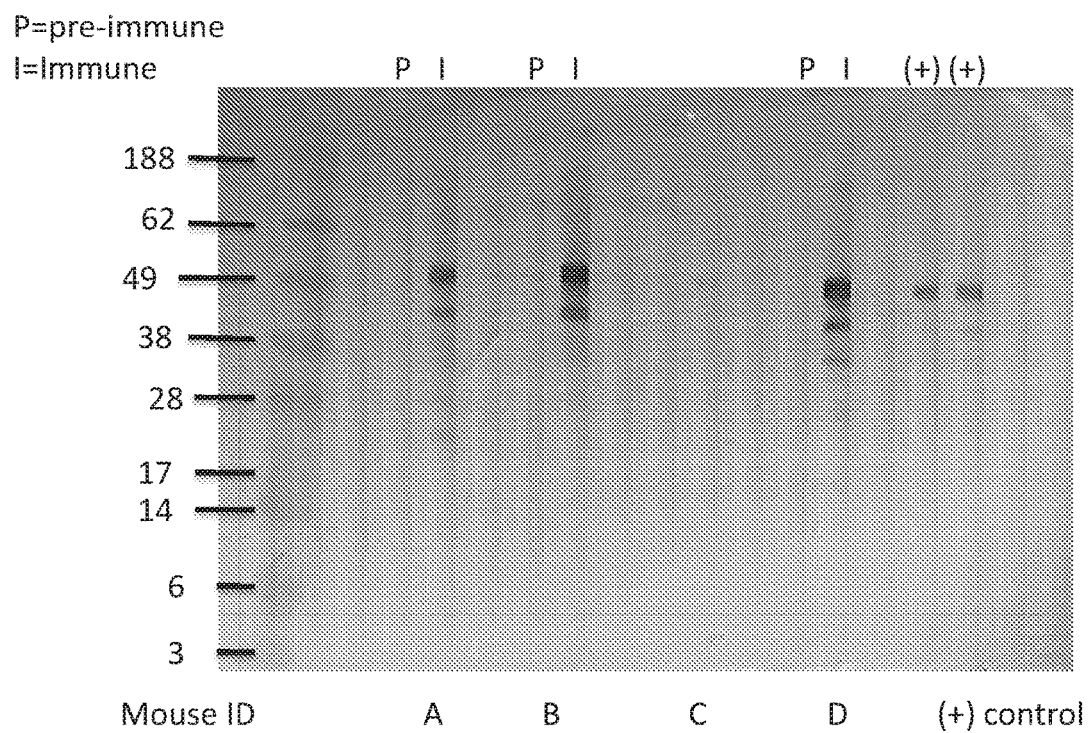

ANTIBODIES TO THE SURFACE OF *TOXOPLASMA GONDII* OOCYSTS AND METHODS OF USE THEREOF

CROSS-REFERENCE

This application claims the benefit of U.S. Provisional Patent Application No. 62/131,098, filed Mar. 10, 2015 and U.S. Provisional Patent Application No. 62/146,063, filed Apr. 10, 2015, which applications are incorporated herein by reference in their entirety.

STATEMENT REGARDING FEDERALLY SPONSORED RESEARCH

This invention was made with government support under Grant No. 1065990, awarded by the National Science Foundation; and government support under Grant No. 1K01RR031487 awarded by the National Institutes of Health. The government has certain rights in the invention.

INTRODUCTION

The *Toxoplasma gondii* parasite causes a disease called toxoplasmosis which can lead to birth defects and neurologic disease in humans and can cause a brain disease, resulting in mortality in southern sea otters (*Enhydra lutris nereis*), a federally listed threatened species. Contaminated water supplies have been implicated as the sources of infection for human toxoplasmosis outbreaks in several countries, including Panama, Brazil, India, French Guyana, and Canada. Infection by *T. gondii* can occur as a result of drinking contaminated water, eating infected and undercooked meat, or through transplacental transmission from mother to fetus. While *T. gondii* is usually associated with subclinical or mild flu-like symptoms in immunocompetent individuals, this parasite causes potentially fatal encephalitis in immunosuppressed patients, as well as abortion and congenital disease in infants born to women who are acutely infected during pregnancy.

Domestic and wild fields are the only known definitive hosts of *T. gondii*, and one cat can shed millions of oocysts in its feces when infected. *Toxoplasma gondii* oocysts are highly resistant to the environment. Oocysts can remain viable in water sources for several years and are reportedly resistant to commonly employed water treatment processes, including chlorination, ozonation, and UV radiation.

There are three infective stages of *T. gondii*: a rapidly dividing invasive tachyzoite, a slowly dividing bradyzoite in tissue cysts, and an environmental stage, the sporozoite, protected inside an oocyst. Tachyzoites are the disseminated form able to invade virtually all vertebrate cell types. Bradyzoites represent the latent form and their resistance to acidic pepsin allows for their transmission through ingestion. Sporozoites are located in mature oocysts. Oocysts are 12- to 13-μm ovoid structures that, after sporulation, contain two sporocysts, each containing four sporozoites. Unsporulated oocysts are excreted in cat feces and sporulation occurs at ambient temperature in the environment.

The oocyst wall is an extremely robust multilayer structure protecting the parasite from mechanical and chemical damage. The oocyst wall is a multi-layered structure that, although robust, permits gaseous exchange essential for sporozoite development. The three layers of the oocyst wall include the outer veil, outer oocyst wall, and the inner oocyst wall. The outer veil is a loose coat that is typically lost when oocysts are excreted in feces. The outer oocyst wall is a 30-70 nm thick coat formed mainly by proteins and carbohydrates. The thicker inner wall is believed to consist of a lipid-rich protein matrix. The oocyst wall itself has been shown in previous studies to be relatively non-immunogenic, particularly as compared to other life cycle stages of *T. gondii* such as tachyzoites and bradyzoites.

Development of antibodies that effectively bind to the *T. gondii* oocyst wall and practical water testing methods to detect the parasite are of significant interest, e.g., to improve water quality monitoring, human public health, and animal testing, as well as to assist in the recovery of the threatened sea otter.

REFERENCES

Robert-Gangneux & Dardé (*Clin. Microbiol. Rev.* (2012) 25(2):264-296)
Fritz et al. (*PLoS One* (2012) 7: e29998)
Fritz et al. *Microbiol Methods* (2012) 88: 47-52)
Fritz et al. (*PLoS One* (2012) 7: e29955)

SUMMARY

The present disclosure provides antibodies that bind the surface of *Toxoplasma gondii* oocysts, methods for using such antibodies and kits and devices for practicing such methods. Such antibodies, methods, kits and devices find use in detection of *T. gondii* oocysts and the isolation of such oocysts from samples including environmental samples, food-based samples, diagnostic samples, and the like.

Aspects of the present disclosure include detecting an intact *Toxoplasma gondii* oocyst in a sample. In certain aspects of the disclosure an intact *T. gondii* oocyst is detected by contacting a sample suspected of containing a *T. gondii* oocyst with an antibody that specifically binds a protein on the outer wall of an intact *T. gondii* oocyst under conditions sufficient to form an immunocomplex of the antibody with the intact *T. gondii* oocyst and detecting the presence or absence of the immunocomplex comprising the antibody.

Aspects of the present disclosure include detecting an intact *Toxoplasma gondii* oocyst in a sample, wherein the sample has not been pre-processed to disrupt the *T. gondii* oocyst. In certain aspects of the disclosure pre-processing comprises mechanical processing and/or chemical processing.

Aspects of the present disclosure include detecting an intact *Toxoplasma gondii* oocyst in a sample, wherein the sample is further suspected of containing an oocyst or cyst of an organism related to *T. gondii* selected from the group consisting of: *Hammondia* spp., *Eimeria* spp., *Isospora* spp., *Giardia* spp. and *Cryptosporidium* spp.

Aspects of the present disclosure include detecting an intact *Toxoplasma gondii* oocyst in a sample using an antibody that specifically binds a protein on the outer wall of an intact *T. gondii* oocyst, wherein the antibody is detectably labeled. In certain aspects of the disclosure the antibody is attached to a support. In certain aspects of the disclosure the antibody is attached to a support and the support is a bead. In certain aspects of the disclosure the antibody is attached to support and the support comprises a surface bound capture agent, and the antibody is attached to the support by binding to the capture agent.

Aspects of the present disclosure include detecting an intact *Toxoplasma gondii* oocyst in a sample using an antibody that specifically binds a protein selected from the group consisting of TyRP1, TyRP2, TyRP3, TyRP4, TyRP5 and TgOWP2.

Aspects of the present disclosure include isolating an intact *Toxoplasma gondii* oocyst in a sample. In certain aspects of the disclosure an intact *T. gondii* oocyst is isolated by contacting a sample suspected of containing a *T. gondii* oocyst with an antibody that specifically binds a protein on the outer wall of an intact *T. gondii* oocyst under conditions sufficient to form an immunocomplex of the antibody with the intact *T. gondii* oocyst and isolating the oocyst based on the binding of the antibody to the intact *T. gondii* oocyst.

Aspects of the present disclosure include isolating an intact *Toxoplasma gondii* oocyst in a sample, wherein the sample has not been pre-processed to disrupt the *T. gondii* oocyst for *T. gondii* oocyst detection. In certain aspects of the disclosure pre-processing comprises mechanical processing and/or chemical processing.

Aspects of the present disclosure include isolating an intact *Toxoplasma gondii* oocyst in a sample, wherein the sample is further suspected of containing an oocyst or cyst of an organism related to *T. gondii* selected from the group consisting of: *Hammondia* spp., *Eimeria* spp., *Isospora* spp., *Giardia* spp. and *Cryptosporidium* spp.

Aspects of the present disclosure include isolating an intact *Toxoplasma gondii* oocyst in a sample using an antibody that specifically binds a protein on the outer wall of an intact *T. gondii* oocyst, wherein the antibody is attached to a support. In certain aspects of the disclosure the support is a bead. In certain aspects of the disclosure the antibody is attached to a support and the support comprises a surface bound capture agent, and the antibody is attached to the support by binding to the capture agent.

Aspects of the present disclosure include isolating an intact *Toxoplasma gondii* oocyst in a sample using an antibody that specifically binds a protein selected from the group consisting of TyRP1, TyRP2, TyRP3, TyRP4, TyRP5 and TgOWP2.

Aspects of the present disclosure include an isolated antibody that specifically binds an epitope within a TyRP protein present in the intact *Toxoplasma gondii* oocyst wall. In certain aspects of the present disclosure a TyRP protein is selected from the group consisting of TyRP1, TyRP2, TyRP3, TyRP4 and TyRP5. In certain aspects of the present disclosure an isolated TyRP antibody comprises a detectable label. In certain aspects of the present disclosure an isolated TyRP antibody is attached to a support. In certain aspects of the present disclosure an isolated TyRP antibody is attached to a bead. In certain aspects of the present disclosure an isolated TyRP antibody is attached to a support and the support comprises a surface bound capture agent, and the antibody is attached to the support by binding to the capture agent.

Aspects of the present disclosure include an isolated antibody that specifically binds an epitope within a TyRP protein present in the intact *Toxoplasma gondii* oocyst wall, wherein the antibody does not bind an epitope of an oocyst or cyst of a related organism selected from the group consisting of: *Hammondia* spp., *Eimeria* spp., *Isospora* spp., *Giardia* spp. and *Cryptosporidium* spp.

Aspects of the present disclosure include an antibody conjugate comprising an isolated antibody that specifically binds an epitope within a TyRP protein present in the intact *Toxoplasma gondii* oocyst wall and a detectable label.

Aspects of the present disclosure include a device for the detection of a *Toxoplasma gondii* oocyst, the device comprising an antibody conjugate comprising an isolated antibody that specifically binds an epitope within a TyRP protein present in the intact *Toxoplasma gondii* oocyst wall and a detectable label.

Aspects of the present disclosure include a kit for the detection of a *Toxoplasma gondii* oocyst, the kit comprising an isolated antibody that specifically binds an epitope within a TyRP protein present in the intact *Toxoplasma gondii* oocyst wall. Certain aspects of the disclosure include kits that comprise an antibody conjugate bound to a detectable label. In certain aspects of the disclosure, a kit includes a capture agent that specifically binds a *T. gondii* oocyst antibody.

Aspects of the present disclosure include an isolated monoclonal antibody that specifically binds an epitope within a TgOWP2 protein present in the intact *Toxoplasma gondii* oocyst wall. In certain aspects of the disclosure an antibody is generated from a recombinant protein expressed in a eukaryotic system having at least 95% amino acid sequence identity to the amino acid sequence set forth in SEQ ID NO: 1. In certain aspects of the disclosure the isolated monoclonal antibody that specifically binds an epitope within a TgOWP2 protein does not bind an epitope of an oocyst or cyst of a related organism selected from the group consisting of: *Hammondia* spp., *Eimeria* spp., *Isospora* spp., *Giardia* spp. and *Cryptosporidium* spp. In certain aspects of the disclosure the isolated monoclonal antibody that specifically binds an epitope within a TgOWP2 protein is detectably labeled. In certain aspects of the disclosure the isolated monoclonal antibody that specifically binds an epitope within a TgOWP2 protein is attached to a support. In certain aspects of the disclosure the isolated monoclonal antibody that specifically binds an epitope within a TgOWP2 protein is attached to a bead. In certain aspects of the disclosure the isolated monoclonal antibody that specifically binds an epitope within a TgOWP2 protein is attached to a support and the support comprises a surface bound capture agent, and the monoclonal antibody is attached to the support by binding to the capture agent.

Aspects of the present disclosure include an antibody conjugate comprising an antibody that specifically binds an epitope within a TgOWP2 protein and a detectable label.

Aspects of the present disclosure include a device for the detection of a *Toxoplasma gondii* oocyst, the device comprising an antibody conjugate comprising an antibody that specifically binds an epitope within a TgOWP2 protein. In certain aspects of the disclosure a device comprises an antibody conjugate comprising an antibody that specifically binds an epitope within a TgOWP2 protein and a detectable label.

Aspects of the present disclosure include a kit for the detection of a *Toxoplasma gondii* oocyst, the kit comprising an antibody that specifically binds an epitope within a TgOWP2 protein. In certain aspects a kit for the detection of a *Toxoplasma gondii* oocyst comprising an antibody that specifically binds an epitope within a TgOWP2 protein further comprises a capture agent that specifically binds the antibody.

BRIEF DESCRIPTION OF THE DRAWINGS

FIG. 6 depicts a lack of reactivity in a TyRP1 immunofluorescence assay (IFA) with disrupted oocyst wall by pre-treatment with bleach ("Bleach Treated"), which removes the outer layer of the oocyst wall but leaves the oocyst wall otherwise intact, (top row, middle panel) in comparison to the reactivity seen in TyRP1 IFA of the untreated oocysts ("Bleach Untreated") contacted with TyRP1 polyclonal antiserum (bottom row, middle panel, arrows). This demonstrates that TyRP1 antibodies bind to the outer layer of the oocyst wall, not the inner layer of the wall or bleach-treated oocyst. Sporocysts, which lack TyRP1 IFA reactivity, are shown alone using autofluorescence under UV excitation (left panels, "Autofluor.") and in the merged images (right panels, "Merge") for reference.

FIG. 7 provides a Western blot performed using pre-immune (P) and immune serum (I) from mice (Mouse ID: A-D) immunized with recombinant TyRP1 (42.6 kDa) (containing a His-tag). The positive control (+) was performed using an anti-His tag antibody. Molecular weight standards are shown in the first lane on the left corresponding to the indicated molecular weights.

DEFINITIONS

Figure 1:
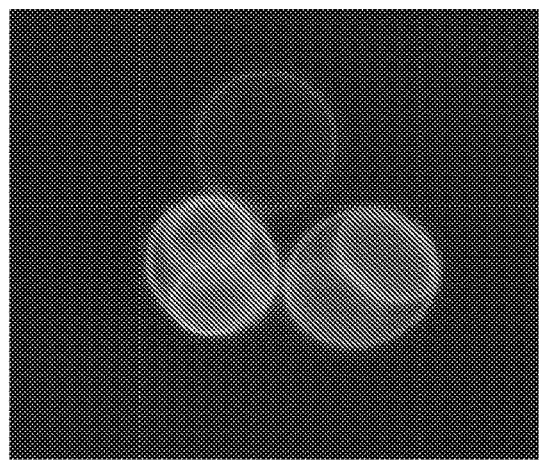
FIG. 1 depicts autofluorescence of the walls of unsporulated (top) and sporulated (bottom) *T. gondii* oocysts (imaged in the UV wavelength 330-385 nm).

The term "recombinant", as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide, means a polypeptide produced by expression from a recombinant polynucleotide. The term recombinant as used with respect to a host cell or a virus means a host cell or virus into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "wild-type" as used herein in reference to biomolecules generally refers to a nucleic acid sequence or an amino acid sequence having a sequence that corresponds to a sequence that is naturally occurring in an organism. However, identifying a biomolecule as wild-type does not indicate that the molecule is necessarily naturally occurring. For example, a non-naturally occurring recombinant polypeptide may be referred to as wild-type when the recombinant polypeptide shares complete sequence identity with the naturally occurring amino acid sequence. Likewise, a non-naturally occurring polynucleotide, e.g., a polynucleotide excluding one or more non-coding nucleic acids, may be referred to as wild-type, e.g., wherein the non-naturally occurring polynucleotide encodes for a polypeptide having an amino acid sequence that shares complete sequence identity with the corresponding naturally occurring amino acid sequence.

The terms "nucleic acid", "nucleic acid molecule" and "polynucleotide" are used interchangeably and refer to a polymeric form of nucleotides of any length, either deoxyribonucleotides or ribonucleotides, or analogs thereof. Non-limiting examples of nucleic acids and polynucleotides include linear and circular nucleic acids, messenger RNA (mRNA), cDNA, recombinant polynucleotides, vectors, probes, primers, single-, double-, or multi-stranded DNA or RNA, genomic DNA, DNA-RNA hybrids, chemically or biochemically modified, non-natural, or derivatized nucleotide bases, oligonucleotides containing modified or non-natural nucleotide bases (e.g., locked-nucleic acids (LNA) oligonucleotides), and interfering RNAs. In some instances, a polynucleotide may be a continuous open reading frame polynucleotide that excludes at least some non-coding sequence from a corresponding sequence present in the genome of an organism.

As used herein, the term "heterologous" used in reference to nucleic acid sequences, proteins or polypeptides, means that these molecules are not naturally occurring in the cell from which the heterologous nucleic acid sequence, protein or polypeptide was derived. For example, the nucleic acid sequence coding for *T. gondii* polypeptide described herein that is inserted into a cell that is not a *T. gondii* cell is a heterologous nucleic acid sequence in that particular context.

The terms "polypeptide" and "protein" are used interchangeably to refer to a polymer of amino acid residues linked by peptide bonds, and for the purposes of the claimed invention, have a minimum length of at least 10 amino acids. Oligopeptides, oligomers multimers, and the like, typically refer to longer chains of amino acids and are also composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 10 amino acids are encompassed by the definition. The terms also include polypeptides that have co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity or maintains particular epitopes to which an antibody directed to the polypeptide may bind. These modifications can be deliberate, as through site-directed mutagenesis, or can be accidental, such as through mutations of hosts that produce the proteins, or errors due to PCR amplification or other recombinant DNA methods.

In the context of amino acid sequence mutants of a polypeptide or an antibody of the instant disclosure, an antibody and/or immunoglobulin chain of the present disclosure can be prepared by introducing appropriate nucleotide changes into a subject nucleic acid encoding a polypeptide of the instant disclosure, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

The term "antibody", as used herein, may refer to whole or intact molecules or fragments thereof and modified and/or conjugated antibodies or fragments thereof that have been modified and/or conjugated. Antibody fragments include but are not limited to antigen-binding fragments (Fab or F(ab), including Fab' or F(ab'), (Fab)$_2$, F(ab')$_2$, etc.), single chain variable fragments (scFv or Fv), "third generation" (3G) molecules, etc. which are capable of binding the epitopic determinant. These antibody fragments retain some ability to selectively bind to the subject antigen, examples of which include, but are not limited to:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab)$_2$, the fragment of the antibody that can be obtained by treating whole antibody with the enzyme pepsin without subsequent reduction;

(4) F(ab)2 is a dimer of two Fab' fragments held together by two disulfide bonds;

(5) Fv, defined as a genetically engineered fragment containing the variable region of the light chain and the variable region of the heavy chain expressed as two chains;

(6) Single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, tetrabodies, etc. which may or may not be polyspecific (see, for example, WO 94/07921 and WO 98/44001) and (7) "3G", including single domain (typically a variable heavy domain devoid of a light chain) and "miniaturized" antibody molecules (typically a full-sized Ab or mAb in which non-essential domains have been removed).

The term "monoclonal antibody" as used herein is not limited to antibodies produced through hybridoma technology. The term "monoclonal antibody" refers to an antibody that is derived from a single clone, including any eukaryotic, prokaryotic, or phage clone and not the method by which it is produced. Monoclonal antibodies useful in connection with the present disclosure can be prepared using a wide variety of techniques including, but not limited to, the use of hybridoma, recombinant, and phage display technologies or a combination thereof.

The term "immunoglobulin", as used herein, refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized, see for instance Fundamental Immunology Ch. 7 (Paul, W., ed., 2nd ed. Raven Press, N.Y. (1989)). Briefly, each heavy chain typically is comprised of a heavy chain variable region (abbreviated as $V_H$) and a heavy chain constant region (abbreviated as $C_H$). The heavy chain constant region typically is comprised of three domains, $C_H1$, $C_H2$, and $C_H3$. Each light chain typically is comprised of a light chain variable region (abbreviated as $V_L$) and a light chain constant region (abbreviated herein as $C_L$). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). In one embodiment, an antibody of the invention at least comprises a $V_L$ domain and a $V_H$ domain.

The term "complementarity determining region" or "CDR", as used herein, refers to amino acid sequences which together define the binding affinity and specificity of a variable fragment (Fv) region of a immunoglobulin binding site.

In some instances, nucleic acid or amino acid sequences, including polypeptides and nucleic acids encoding polypeptides, are referred to based on "sequence similarity", e.g., as compared to one or more reference sequences. In other instances, a mutant or variant sequence may be referred to based on comparison to one or more reference sequences. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Where necessary or desired, optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

The terms "infecting", "infect", and the like, refer to the introduction of material into a living organism or cell, including e.g., a cell culture, in order to alter the organism or cell in some way. For example, a cell or culture of cells may be infected with a virus and the virus itself may be introduced into the cell or the virus may inject genetic material into the cell. In some instances, a culture may be referred to as infected at the time the infective agent is added to the culture. In other instances, a culture of cells may only be referred to as infected when it is clear that the infective agent is transferring material into the cells of the culture, e.g., through observation or some other assay. Infection may proceed through a natural process or may be achieved through the use of artificial process or may make use of both natural and artificial process for introducing infectious material. In some instances, where artificial processes for infecting cells with introduced genetic material, e.g., lipofection, electroporation, etc., such infections may be referred to as transfections.

The terms "virus particles", "virus", and the like, refer to an infectious viral agent, including, e.g., baculovirus particles, lentivirus particles, adenovirus particles, and the like. Virus and virus particles may be naturally occurring, recombinant, engineered, or synthetic.

The term "vector" refers to a nucleic acid molecule capable of transporting or mediating expression of a heterologous nucleic acid to which it has been linked to a host cell; a plasmid is a species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self-replicating extrachromosomal vectors or vectors which integrates into a host genome.

The term "incubating" refers to exposing an agent, a reaction, a cell, a cell culture, or living organism, etc. to conditions that are permissive for or promote a desired result or change in the agent, reaction, cell, cell culture, or living organism. For example, a culture of cells may be incubated in environmental conditions permissive for cell growth thus resulting the growth and/or expansion of the culture of cells. Incubation conditions may vary for a particular item based on the desired result of the incubation. For example, incubation conditions for cell growth may, in some instances, differ from incubation conditions for cellular expression of a heterologous gene, however, in some instances incubation conditions for different purposes may, in fact, be the same or may be overlapping. Incubating or incubating in effective conditions and/or permissive conditions may also refer to the amount of time necessary for a particular process to take place. For example, incubation of particular reaction under conditions permissive for the reaction to take place may also, in some instances, refer to incubation under permissive conditions for a length of time sufficient for the reaction to take place.

The terms "purifying", "isolating", and the like, refer to the removal of a desired substance, e.g., a recombinant protein, from a solution containing undesired substances, e.g., contaminates, or the removal of undesired substances from a solution containing a desired substances, leaving behind essentially only the desired substance. In some instances, a purified substance may be essentially free of other substances, e.g., contaminates. Purifying, as used herein, may refer to a range of different resultant purities, e.g., wherein the purified substance makes up more than 80% of all the substance in the solution, including more than 85%, more than 90%, more than 91%, more than 92%, more than 93%, more than 94%, more than 95%, more than 96%, more than 97%, more than 98%, more than 99%, more than 99.5%, more than 99.9%, and the like. As will be understood by those of skill in the art, generally, components of the solution itself, e.g., water or buffer, or salts are not considered when determining the purity of a substance.

The terms "detection reagents", "reporters", "reporter binding members" and the like, refer to reagents useful in indicating the presence of a reaction, including an enzymatic reaction or a binding reaction. Detection reagents, e.g., of a signal producing system, include but are not limited to detectable labels and reporter binding members having been detectably labeled. Suitable detectable labels for use in the methods disclosed herein include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, Alexa Fluor® dyes, and the like), radiolabels (e.g., $^3$H, $^{125}$I, $^{35}$S, $^{14}$C, $^{13}$C or $^{32}$P), enzymes (e.g., horseradish peroxidase, alkaline phosphatase and others commonly used in an ELISA), colorimetric labels such as colloidal gold or colored glass or plastic (e.g., polystyrene, polypropylene, latex beads), magnetic substrates such as magnetic beads, charged substrates, and the like. See, e.g., the Handbook of Fluorescent Probes and Research Chemicals (6th Ed., Molecular Probes, Inc., Eugene, Oreg.). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels may be detected by simply visualizing the colored label. Magnetic labels or charged labels can be detected using a device configured to detect the movement of a particle, e.g., the movement of a magnetic or charged particle through an magnetic or electric field. In some instances a nucleic acid tag serve as a detectable label and such nucleic acid tags may be detected by amplification of the nucleic acid tag and/or sequencing of the tag or amplification product of the tag. Such detectable labels and detection reactions as described herein may produce a detectable signal.

The term "detecting" as used herein refers to the act of observing, e.g., directly or indirectly, or receiving an indication of the presence of detectable signal. In some instances where detecting involves the observation of a detectable signal, a method as described herein may make use of one or more observation devices. Observation devices that may be used in detecting a signal produced from a signal producing system include but are not limited to detection devices commonly used in research laboratories, e.g., high sensitivity cameras, microscopes, ultraviolet lights, etc. In certain instances the signal produced may require the use of such an observation device to facilitate detection. In certain instances the signal produced from a signal producing system may not be directly observed and may instead be detected through the use of a detector or scanner. In some instances although the signal is visible a detector or scanner may be used in order to quantify the signal, e.g., allowing quantitative analysis of *T. gondii* oocysts. Detectors and scanners that find use in the devices and methods of the present disclosure include but are not limited to, e.g., film based detectors, photospectrometers, photodetectors, laser scanners, flow cytometers, photo scanners, document scanners, etc.

The terms "control", "control reaction", "control assay", and the like, refer to a reaction, test, or other portion of an experimental or diagnostic procedure or experimental design for which an expected result is known with high certainty, e.g., in order to indicate whether the results obtained from associated experimental samples are reliable, indicate to what degree of confidence associated experimental results indicate a true result, and/or to allow for the calibration of experimental results. For example, in some instances, a control may be a "negative control" such that an essential component of the assay is excluded from the negative control reaction such that an experimenter may have high certainty that the negative control reaction will not produce a positive result. In some instances, a control may be "positive control" such that all components of a particular assay are characterized and known, when combined, to produce a particular result in the assay being performed such that an experimenter may have high certainty that the positive control reaction will not produce a positive negative result.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" includes a plurality of such antibodies and reference to "the oocyst" includes reference to one or more oocysts and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

General Techniques

Unless specifically defined otherwise, all technical and scientific terms used herein shall be taken to have the same meaning as commonly understood by one of ordinary skill in the art (e.g., in cell culture, molecular genetics, antibody technology, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The present disclosure provides antibodies and fragments thereof that bind *T. gondii* oocysts and methods for using antibodies and fragments thereof that bind *T. gondii* oocysts, generally involving the detection of *T. gondii* oocysts in a sample and/or the isolation of *T. gondii* oocysts from a sample. The present disclosure also provides devices that use antibodies or fragments thereof that bind *T. gondii* oocysts and kits that include antibodies or fragments thereof that bind to *T. gondii* oocysts.

Antibodies

The instant disclosure provides antibodies or fragments thereof that bind to the surface of a *T. gondii* oocyst. Such antibodies or fragments thereof bind components of the oocyst wall, including components of the outer oocyst wall, and epitopes found within such components. In some instances, components to which an antibody or fragment thereof binds may be referred to as an antigen. Antigens of interest include oocyst wall antigens, including outer oocyst wall antigens. Antibodies or fragments thereof of the instant disclosure may be produced from purified antigens which may be purified recombinantly produced antigens, e.g., by exposing a host animal or antibody production system to a purified antigen or purified recombinantly produced antigen.

In some embodiments, antibodies of the instant disclosure are produced from antigens that are recombinantly produced, e.g., as described herein. In some embodiments, antibodies of the instant disclosure are generated from recombinant polypeptides that share sequence identity to a wild-type amino acid sequence of a *T. gondii* protein. The degree of sequence identity shared between a recombinant polypeptide used in the production of an antibody as described herein and a wild-type *T. gondii* polypeptide will vary and in some instances may be up to 100%. In instances where the degree of sequence identity shared between a recombinant polypeptide used in the production of an antibody as described herein and a wild-type *T. gondii* polypeptide is less than 100% the recombinant polypeptide may be referred to as a mutant recombinant polypeptide. The degree of sequence identity shared between a mutant recombinant polypeptide used in the production of an antibody as described herein and a wild-type *T. gondii* polypeptide will vary and in some instances may range from less than 70% to 99% or more including but not limited to, e.g., at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, etc. Antigens and polypeptides from which antibodies of the instant disclosure may be derived are discussed in further detail below.

In certain embodiments, an antigen is produced through recombinant or other means and the antibody is generated in a host animal, e.g., through immunization of a host animal with the recombinant or synthetic antigen. Host animals that may be immunized with an antigen of the instant disclosure in order to generate antibodies to the antigen include but are not limited to, e.g., mouse, rat, rabbit, guinea pig, chicken, cat, dog, goat, sheep, donkey, cow, horse, camel, llama, monkey, ape, etc. In some instances, following generation of an antibody in a host animal, serum is collected and serum containing the antibody may be subsequently used directly. In other instances, following generation of an antibody in a host animal, serum is collected and serum containing the antibody may be subsequently used to purify the antibody such that the generated antibody is purified or isolated from the serum. Methods of generating, isolating, purifying antibodies through the immunization of host animal are well known in the art.

In some instances, an antibody or immunoglobulin of interest may be a recombinant antibody or immunoglobulin chain. In the context of an antibody or immunoglobulin chain, recombinant antibody or recombinant immunoglobulin chain refers to the antibody or immunoglobulin chain when produced by a cell, or in a cell-free expression system, in an altered amount or at an altered rate compared to its native state. In one embodiment, the cell is a cell that does not naturally produce the antibody or immunoglobulin chain. However, the cell may be a cell which comprises a non-endogenous gene that causes an altered, preferably increased, amount of the polypeptide to be produced. A recombinant antibody or immunoglobulin chain of the invention includes polypeptides which have not been separated from other components of the transgenic (recombinant) cell, or cell-free expression system, in which it is produced, and an antibody or immunoglobulin chain produced in such cells or cell-free systems which are subsequently purified away from at least some other components.

Polypeptides

Polypeptides of the instant disclosure include antigens and antigen binding fragments as described herein. For example, an antigen used in generating an antibody for use in binding a *T. gondii* oocyst may be a *T. gondii* oocyst polypeptide, including, e.g., a *T. gondii* oocyst wall polypeptide, including *T. gondii* outer oocyst wall polypeptide or a *T. gondii* inner oocyst wall polypeptide. In one embodiment, the *T. gondii* oocyst polypeptide is a recombinant *T. gondii* oocyst polypeptide, including a recombinant *T. gondii* outer oocyst wall polypeptide or a recombinant *T. gondii* inner oocyst wall polypeptide.

Without being bound by theory, antibodies of the instant disclosure generated against polypeptides present on the intact outer surface or other easily accessible surface of the *T. gondii* oocyst allow for use without treatment of the *T. gondii* oocyst or sample suspected of containing *T. gondii* oocyst with agents necessary to expose antigens that may be present on inner surfaces of the *T. gondii* oocyst.

In some instances, a recombinant *T. gondii* outer oocyst wall polypeptide may be a *T. gondii* oocyst outer wall protein (TgOWP). In one embodiment, an antibody as described herein is derived from a recombinant polypeptide that shares at least 75% sequence identity with the TgOWP of SEQ ID NO:1. In one embodiment, an antibody as described herein is derived from a recombinant polypeptide that shares at least 80% sequence identity with the TgOWP of SEQ ID NO:1. In one embodiment, an antibody as described herein is derived from a recombinant polypeptide that shares at least 85% sequence identity with the TgOWP of SEQ ID NO:1. In one embodiment, an antibody as described herein is derived from a recombinant polypeptide that shares at least 90% sequence identity with the TgOWP of SEQ ID NO:1. In one embodiment, an antibody as described herein is derived from a recombinant polypeptide that shares at least 95% sequence identity with the TgOWP of SEQ ID NO:1. In one embodiment, an antibody as described herein is derived from a recombinant polypeptide that shares 100% sequence identity with the TgOWP of SEQ ID NO:1. In one embodiment, In one embodiment, an antibody as described herein is derived from a full length TgOWP recombinant polypeptide of SEQ ID NO:1.

The amino acid sequence of the TgOWP of SEQ ID NO:1 and the nucleic acid sequence encoding the amino acid sequence are provided below. In some instances, the TgOWP of SEQ ID NO:1 may be referred to herein as Tg25 or Tg25.22 and elsewhere as TgOWP2.

TgOWP (Tg25) Amino Acid Sequence:

(SEQ ID NO: 1)
MPTICSKIICALSVLLATTAHVPGMPALASTDATIMKKAPGTYPAPPPDP
TRARCKCPFGFEKMDKSCVKKEAAGQPEAICQSGVLEDGKCRTRAAEAFR
CPDGFETICDANSTAKSKCCRRTESQEINFKCAEGTTETIDGDCKRLKQF
PPSHECPLGYRYDERYCVRTEPGHVVPACGVESQLTAHNSCLSIAPGEIV
YECPVGFHCASNAKNSDFCKSCKRRELEPVSCECDAGTVESDGLCYQAEE
YHECFDKIKKNVVPTEVVDKDEDEKLDKKKDKKCETTRSKCSCRAGFNLV
CKGKECHCVKEESAAVVRRCLGFDDGSGNCVRHLETAPVYQCGEGQECEI
VGKKECKCVYKIRKDSTINCGDGVLIGSDCFSVEHIPKTRHCQDGFDVAC
RRSECQCERNVFTRRVLTCDAEAAKKSEGCASLSEPEFICKEGQLINGNC
VRLSYTVELCEA TgOWP (Tg25) Nucleic Acid Coding Sequence:

(SEQ ID NO: 2)
ATGCCGACTATCTGTTCAAAGATCATTTGTGCGTTGTCTGTTTTGCTTGC
AACAACAGCCCACGTTCCGGGAATGCCTGCTTTGGCATCGACCGATGCCA
CTATCATGAAGAAGGCTCCGGGTACCTATCCAGCACCTCCACCAGATCCA
ACAAGAGCCAGGTGCAAGTGCCCGTTCGGCTTTGAGAAAATGGACAAATC
ATGTGTGAAGAAGGAGGCTGCAGGACAGCCAGAGGCTATCTGCCAATCTG
GTGTTCTGGAGGACGGAAAATGCAGAACCCGGGCTGCTGAAGCCTTTCGC
TGTCCTGACGGCTTTGAGACTATCTGTGACGCAAACTCTACAGCGAAGTC
GAAGTGCTGCCGCCGAACAGAGTCACAAGAAATCAATTTTAAATGTGCCG
AAGGAACAACGGAGACTATTGACGGTGACTGCAAGCGCTTGAAGCAGTTT
CCGCCAAGTCATGAGTGTCCCTTGGGCTATCGGTACGATGAAAGGTACTG
CGTCAGGACAGAGCCCGGACACGTTGTGCCTGCATGTGGCGTGGAGAGTC
AGTTAACGGCGCACAACTCTTGCCTCTCGATTGCCCCTGGCGAGATCGTG
TATGAGTGCCCTGTAGGGTTTCATTGTGCCTCGAATGCGAAGAACTCCGA
CTTTTGCAAAAGCTGCAAGAGGAGAGAGTTGGAGCCTGTCAGTTGTGAGT
GTGACGCCGGCACCGTAGAAAGTGATGGCCTCTGCTACCAGGCCGAAGAG
TACCATGAGTGTTTTGACAAGATAAAGAAAAATGTGGTACCTACCGAGGT
CGTCGACAAGGACGAAGATGAGAAATTAGACAAGAAAAAGGACAAGAAGT
GTGAAACAACAAGGTCGAAATGCTCATGCCGCGCTGGCTTCAATCTCGTG
TGCAAGGGAAAGGAGTGTCACTGTGTGAAGGAAGAATCGGCTGCAGTTGT
AAGGCGTTGCCTCGGGTTTGACGATGGTTCCGGCAACTGTGTGCGCCACT
TGGAGACGGCTCCCGTTTACCAATGCGGCGAAGGACAGGAATGCGAAATC
GTGGGGAAAAAGAGTGCAAATGTGTCTACAAGATCCGAAAAGACTCTAC
GATAAATTGCGGCGACGGCGTCCTGATAGGGAGCGACTGCTTTTCGGTGG
AGCACATTCCGAAAACACGACATTGTCAGGATGGCTTCGATGTTGCCTGT
CGCAGATCGGAATGTCAATGCGAACGAAATGTTTTCACACGCAGAGTGCT
GACGTGTGATGCTGAGGCGGCCAAAAAATCTGAAGGCTGTGCAAGTTTAT
CAGAGCCGGAATTCATCTGCAAAGAGGGTCAATTGATCAACGGAAATTGC
GTTAGACTGTCATACACAGTTGAGTTGTGCGAAGCGTGA

The genomic locus of Tg25 is provided below with the non-coding sequence (e.g., introns indicated as lower case:

(SEQ ID NO: 3)
accacaccttaacattctagaatctgaatttgtttgtcacaacatcgcta
ctttagtaatcgcacatcgtaacgATGCCGACTATCTGTTCAAAGATCAT
TTGTGCGTTGTCTGTTTTGCTTGCAACAACAGCCCACGTTCCGGGAATGC
CTGCTTTGGCATCGACCGATGCCACTATCATGAAGAAGGCTCCGGGTACC
TATCCAGCACCTCCACCAGATCCAACAAGAGCCAGGTGCAAGTGCCCGTT
CGGCTTTGAGAAAATGGACAAATCATGTGTGAAGAAGGAGGCTGCAGGAC
AGCCAGAGgtaaaacgggtaccgctcctcaaaacagataattgctgatca
acagttttacagGCTATCTGCCAATCTGGTGTTCTGGAGGACGGAAAATG
CAGAACCCGGGCTGCTGAAGCCTTTCGCTGTCCTGACGGCTTTGAGACTA
TCTGTGACGCAAACTCTACAGCGAAGTCGAAGTGCTGCCGCCGAACAGAG
TCACAAGAAATCAATTTTAAATGTGCCGAAGGAACAACGGAGACTATTGA
CGGTGACTGCAAGCGCTTGAAGCAGTTTCCGCCAAGTCATGAGTGTCCCT
TGGGCTATCGGTACGATGAAAGGTACTGCGTCAGGACAGAGCCCGGACAC
GTTGTGCCTGCATGTGGCGTGGAGAGTCAGTTAACGGCGCACAACTCTTG
CCTCTCGATTGCCCCTGGCGAGATCGTGTATGAGTGCCCTGTAGGGTTTC
ATTGTGCCTCGAATGCGAAGAACTCCGACTTTTGCAAAAGCTGCAAGAGG
AGAGAGTTGGAGCCTGTCAGTTGTGAGTGTGACGCCGGCACCGTAGAAAG
TGATGGCCTCTGCTACCAGGCCGAAGAGTACCATGAGTGTTTTGACAAGA
TAAAGAAAAATGTGGTACCTACCGAGGTCGTCGACAAGGACGAAGATGAG
AAATTAGACAAGAAAAAGGACAAGAAGTGTGAAACAACAAGGTCGAAATG
CTCATGCCGCGCTGGCTTCAATCTCGTGTGCAAGGGAAAGGAGTGTCACT
GTGTGAAGGAAGAATCGGCTGCAGTTGTAAGGCGTTGCCTCGGGTTTGAC
GATGGTTCCGGCAACTGTGTGCGCCACTTGGAGACGGCTCCCGTTTACCA
ATGCGGCGAAGGACAGGAATGCGAAATCGTGGGGAAAAAGAGTGCAAAT
GTGTCTACAAGATCCGAAAAGACTCTACGATAAATTGCGGCGACGGCGTC
CTGATAGGGAGCGACTGCTTTTCGGTGGAGCACATTCCGAAAACACGACA
TTGTCAGGATGGCTTCGATGTTGCCTGTCGCAGATCGGAATGTCAATGCG
AACGAAATGTTTTCACACGCAGAGTGCTGACGTGTGATGCTGAGGCGGCC
AAAAAATCTGAAGGCTGTGCAAGTTTATCAGAGCCGGAATTCATCTGCAA
AGAGgtaggccggtcatcattgtttatacaaaacgcaaaaaaatgcttgc
gttttttcagGGTCAATTGATCAACGGAAATTGCGTTAGACTGTCATACA
CAGTTGAGTTGTGCGAAGCGTGAcctagtgtttcaaaatcaaattcggac
actcctgtgctggagcaaatgactttgttgttgtatattggtaccatata
aaggactcgcgacacaccgatccatactgtaacatggtatggacatcttg
cattttcctctaggaaagagtgacaacacgagagagaaaaatagcgcttt
caagctggcaaactgccattccctttaccttggtatccgcggagagaaag
ccgcttcttcagcggtatctttcaggtgtggccaattggtcaggaatatc
tgagacattccgttcaattagaccagacccagtctcattagcgctgtgaa -continued
```
ttgccgcggattgaccccgttccgtttacccgttcggccgactatgctgt actgccttaatggccgctcgctgcgacttcacacgttccaaaacgtctgg ctcgttcatgtctggccgcagaatccgatgcataacgcatgatccagcga acgccgatgcaaaagcgacgaacagagagagagcaaattctccacgggtg agacctgctggcatcttgccgaattaccgacgggttctttccggttaagc ctcacttggtctttgctgaagcaggctggtatgttgtcggaagatatgga cacaacagaatagtaagagaacctggagctagtgaaacagaaatctgtaa agcgtcccaaaaccagcatgcctgaccgggaaatggccctctagcacc gagacagcaaggagcacgttaagcgtgatctgattgtggaatgtacaaaa catgtg,
```

In certain embodiments, a Tg25 polypeptide, e.g., as used to generate an antibody as described herein, may be recombinantly derived from the *T. gondii* M4 strain. In other instances, a Tg25 polypeptide, e.g., as used to generate an antibody as described herein, may be recombinantly derived from the *T. gondii* ME49 strain.

In some instances, an antibody directed to a Tg25 polypeptide specifically binds to an epitope of the Tg25 polypeptide. In some instances, an antibody directed to a Tg25 polypeptide specifically binds to a linear epitope of the Tg25 polypeptide. In some instances, an antibody directed to a Tg25 polypeptide specifically binds to a conformational epitope of the Tg25 polypeptide. Determination of the particular epitope to which an anti-Tg25 polypeptide binds may be determined empirically through epitope mapping performed by one or more techniques including but not limited to, e.g., x-ray crystallography, olio-peptide scanning (i.e. pepscan), site-directed mutagenesis, mutagenesis mapping, hydrogen-deuterium exchange, phage display, limited proteolysis, and the like.

In some instances, a recombinant *T. gondii* outer oocyst wall polypeptide may be a *T. gondii* Tyrosine-Rich Protein (TyRP). In one embodiment, an antibody as described herein is derived from a recombinant polypeptide that shares at least 75% sequence identity with TyRP1 of SEQ ID NO:4. In one embodiment, an antibody as described herein is derived from a recombinant polypeptide that shares at least 80% sequence identity with TyRP1 of SEQ ID NO:4. In one embodiment, an antibody as described herein is derived from a recombinant polypeptide that shares at least 85% sequence identity with TyRP1 of SEQ ID NO:4. In one embodiment, an antibody as described herein is derived from a recombinant polypeptide that shares at least 90% sequence identity with TyRP1 SEQ ID NO:4. In one embodiment, an antibody as described herein is derived from a recombinant polypeptide that shares at least 95% sequence identity with TyRP1 of SEQ ID NO:4. In one embodiment, an antibody as described herein is derived from a recombinant polypeptide that shares 100% sequence identity with TyRP1 of SEQ ID NO:4. In one embodiment, an antibody as described herein is derived from a full length TyRP1 recombinant polypeptide of SEQ ID NO:4.

TyRP1 Amino Acid Sequence:

```
                                        (SEQ ID NO: 4)
MKAAVALSLFGLTLALPMVALAEEMSSEMVDSVDMLEMEDVSVQETQELS

EESSTAPMRYLEEDSTDDIFLIPETTSPIRVLGKKNRAVYVAAPKKYVAP

VVQKKAPVAHSKYSAPAPSKKMHAPAKKAPVIMSSKYAPAPASKKYTQAA

PSKKYRRLAPVPEMSEEESTATSISDIEVDDEERELKKNSGYYVAYTPVV

ASPYCSVGSSCARYLGEEQDMNEEFMSEEEEAVYEQSAEERSLGKKSRAV

YVAPAPKKYVAPAPQKKVAAPVYRAASMHKKAEPVVQMKATPVQKKAAPV

AHKKTPAFPSKKYHQAMSSSKYTPITTLSKKRRLAAQEDVAVEEESTATE

TETEEEERDLKKRGTYYYPVAAYPVVATPYCSTGGACY,.
```

TyRP1 Nucleic Acid Coding Sequence:

```
                                        (SEQ ID NO: 5)
ATGAAGGCAGCCGTTGCTCTATCTCTTTTCGGGCTTACTCTGGCTCTCCC

AATGGTAGCTCTGGCAGAGGAAATGAGCAGCGAAATGGTTGACAGTGTTG

ATATGCTCGAGATGGAGGATGTTTCCGTTCAGGAGACCCAGGAACTGTCA

GAGGAATCTAGCACCGCGCCCATGCGTTATCTTGAAGAAGATAGCACCGA

CGACATTTTCCTCATTCCTGAGACCACCTCTCCCATCCGCGTTCTGGGCA

AGAAAAACCGTGCCGTTTACGTCGCTGCCCCCAAGAAGTATGTGGCTCCT

GTTGTGCAGAAGAAGGCCCCAGTTGCCCACTCCAAGTACTCGGCACCCGC

CCCGTCCAAGAAAATGCACGCGCCTGCCAAGAAGGCCCCAGTTATTATGT

CGTCCAAGTACGCGCCTGCCCCCGCCTCGAAAAAGTACACGCAAGCTGCC

CCGTCGAAGAAGTATCGCCGACTTGCGCCCGTTCCCGAGATGTCCGAAGA

GGAATCGACTGCAACTTCCATCTCGGACATCGAAGTCGATGATGAAGAAC

GTGAGCTGAAGAAGAACAGTGGCTACTATGTGGCGTACACCCCGGTCGTT

GCTAGCCCGTACTGCAGTGTCGGCTCATCTTGTGCTCGCTACCTCGGTGA

AGAGCAAGATATGAACGAGGAGTTCATGAGCGAGGAAGAGGAGGCTGTGT

ATGAGCAGAGTGCTGAAGAGCGCTCCTTGGGAAAGAAGAGCCGTGCGGTT

TACGTGGCCCCTGCCCCAAAAAAGTACGTGGCCCCCGCTCCTCAAAAGAA

GGTCGCTGCTCCGGTGTACCGTGCAGCCTCTATGCATAAGAAGGCTGAGC

CGGTTGTTCAGATGAAGGCCACGCCTGTTCAGAAGAAGGCCGCGCCTGTT

GCTCATAAGAAGACCCCCGCTTTCCCGTCGAAGAAATACCATCAGGCTAT

GTCGTCATCCAAATACACTCCTATCACTACTCTTAGCAAGAAGCGCCGCC

TGGCAGCTCAGGAAGATGTTGCTGTCGAGGAGGAGTCCACTGCGACTGAA

ACTGAGACAGAGGAAGAGGAGCGTGACCTGAAAAAACGTGGAACATACTA

CTACCCGGTTGCTGCCTACCCGGTCGTCGCCACCCCGTACTGCAGCACCG

GTGGTGCGTGCTACTAA.
```

In certain embodiments, a TyRP1 polypeptide, e.g., as used to generate an antibody as described herein, may be recombinantly derived from the *T. gondii* M4 strain. In other instances, a TyRP1 polypeptide, e.g., as used to generate an antibody as described herein, may be recombinantly derived from the *T. gondii* ME49 strain.

In some instances, an antibody directed to a TyRP1 polypeptide specifically binds to an epitope of the TyRP1 polypeptide. In some instances, an antibody directed to a TyRP1 polypeptide specifically binds to a linear epitope of the TyRP1 polypeptide. In some instances, an antibody directed to a TyRP1 polypeptide specifically binds to a conformational epitope of the TyRP1 polypeptide. Determination of the particular epitope to which an anti-TyRP1 polypeptide binds may be determined empirically through epitope mapping performed by one or more techniques including but not limited to, e.g., x-ray crystallography, olio-peptide scanning (i.e. pepscan), site-directed mutagenesis, mutagenesis mapping, hydrogen-deuterium exchange, phage display, limited proteolysis, and the like.

In one embodiment, an antibody as described herein is derived from a recombinant polypeptide that shares at least 75% sequence identity with TyRP2 of SEQ ID NO:6. In one embodiment, an antibody as described herein is derived from a recombinant polypeptide that shares at least 80% sequence identity with TyRP2 of SEQ ID NO:6. In one embodiment, an antibody as described herein is derived from a recombinant polypeptide that shares at least 85% sequence identity with TyRP2 of SEQ ID NO:6. In one embodiment, an antibody as described herein is derived from a recombinant polypeptide that shares at least 90% sequence identity with TyRP2 SEQ ID NO:6. In one embodiment, an antibody as described herein is derived from a recombinant polypeptide that shares at least 95% sequence identity with TyRP2 of SEQ ID NO:6. In one embodiment, an antibody as described herein is derived from a recombinant polypeptide that shares 100% sequence identity with TyRP2 of SEQ ID NO:6. In one embodiment, an antibody as described herein is derived from a full length TyRP2 recombinant polypeptide of SEQ ID NO:6.

TyRP2 Amino Acid Sequence:

(SEQ ID NO: 6)
MKGFIKILLLLGLLAVTTRTVAQETEEAKLTSDSEKVAASSNLTPDNALA

GAPQNEVAATEKVTDEKGSGEEAAEPDEDKKDDGEATNNEDEQKGDDDAK

DHADEQKDDKKQGNDEHSSQKLSFIECDCRKKRVRGTGAPCSCADLVKEA

FRHSLLPWFLPGFFPRQESEGSTMKPRLSGRQRLLGLGNLFGGYYPGYGY

GYPGYGYGYGYGYPGYGYPGYGFGGFGPGFGVGFTF.

TyRP2 Nucleic Acid Coding Sequence:

(SEQ ID NO: 7)
ATGAAAGGCTTCATCAAGATTCTTCTGCTCCTTGGCCTCCTGGCCGTGAC

AACCAGGACCGTCGCTCAAGAGACTGAGGAGGCGAAGTTGACGAGTGACT

CCGAAAAGGTTGCCGCGTCCAGCAACCTCACTCCTGATAATGCGCTCGCT

GGCGCTCCACAGAATGAGGTGGCTGCCACAGAAAAGGTGACAGACGAGAA

AGGCAGCGGTGAAGAGGCTGCGGAACCCGACGAGGACAAGAAAGACGATG

GCGAGGCAACGAACAATGAGGACGAACAGAAAGGCGATGACGATGCAAAG

GATCACGCTGATGAACAGAAAGACGATAAGAAGCAAGGTAATGATGAACA

CTCCTCCCAGAAACTCTCGTTTATCGAATGCGACTGCAGAAAAAAGCGCG

TTCGCGGCACCGGCGCTCCCTGTTCTTGTGCTGACCTTGTGAAAGAAGCG

TTCCGCCACAGCCTGCTGCCTTGGTTTCTCCCTGGATTCTTTCCGAGACA

AGAGTCGGAAGGTAGTACGATGAAACCGCGCCTCTCGGGCCGTCAACGGC

TTCTGGGACTCGGCAATCTTTTCGGTGGATACTATCCCGGCTACGGCTAC

GGATATCCTGGATATGGCTACGGATATGGCTATGGCTATCCCGGCTACGG

CTATCCTGGATACGGCTTCGGAGGCTTCGGTCCTGGTTTTGGTGTTGGCT

TCACATTCTAA.

In certain embodiments, a TyRP2 polypeptide, e.g., as used to generate an antibody as described herein, may be recombinantly derived from the *T. gondii* M4 strain. In other instances, a TyRP2 polypeptide, e.g., as used to generate an antibody as described herein, may be recombinantly derived from the *T. gondii* ME49 strain.

In some instances, an antibody directed to a TyRP2 polypeptide specifically binds to an epitope of the TyRP2 polypeptide. In some instances, an antibody directed to a TyRP2 polypeptide specifically binds to a linear epitope of the TyRP2 polypeptide. In some instances, an antibody directed to a TyRP2 polypeptide specifically binds to a conformational epitope of the TyRP2 polypeptide. Determination of the particular epitope to which an anti-TyRP2 polypeptide binds may be determined empirically through epitope mapping performed by one or more techniques including but not limited to, e.g., x-ray crystallography, olio-peptide scanning (i.e. pepscan), site-directed mutagenesis, mutagenesis mapping, hydrogen-deuterium exchange, phage display, limited proteolysis, and the like.

In one embodiment, an antibody as described herein is derived from a recombinant polypeptide that shares at least 75% sequence identity with TyRP3 of SEQ ID NO:8. In one embodiment, an antibody as described herein is derived from a recombinant polypeptide that shares at least 80% sequence identity with TyRP3 of SEQ ID NO:8. In one embodiment, an antibody as described herein is derived from a recombinant polypeptide that shares at least 85% sequence identity with TyRP3 of SEQ ID NO:8. In one embodiment, an antibody as described herein is derived from a recombinant polypeptide that shares at least 90% sequence identity with TyRP3 SEQ ID NO:8. In one embodiment, an antibody as described herein is derived from a recombinant polypeptide that shares at least 95% sequence identity with TyRP3 of SEQ ID NO:8. In one embodiment, an antibody as described herein is derived from a recombinant polypeptide that shares 100% sequence identity with TyRP3 of SEQ ID NO:8. In one embodiment, an antibody as described herein is derived from a full length TyRP3 recombinant polypeptide of SEQ ID NO:8.

TyRP3 Amino Acid Sequence:

(SEQ ID NO: 8)
MTRSRVLCSVALLASTQLLSWAQADDPVVSVEELIRSEEPGTISASSAGD

YGLIEDPEDTREMSHHRRYSYPASYVLPSPVYYPRSHYYPRYLVNQKAFK

EDDMQTVDDQEEMSPVAPPAGERDLSHRRHESPAPYGYYYSPAEYYTPKH

YVGSPYPRYLKEARRAAVVDKSAAAQSKFMAASRKVRNMGHRRYGYYHVP

LPYYSSYYGYRNSPYGYVRYLY.

TyRP3 Nucleic Acid Coding Sequence:

(SEQ ID NO: 9)
ATGACAAGGTCACGTGTGCTGTGCAGCGTAGCGCTATTGGCGTCTACGCA

ATTGCTGTCCTGGGCCCAAGCTGATGATCCGGTCGTGTCCGTCGAGGAGC

TCATCCGGTCGGAAGAACCAGGCACAATTTCCGCAAGCAGTGCGGGAGAC

TATGGCCTTATAGAGGACCCAGAAGATACAAGGGAGATGTCTCATCACCG

GAGGTACTCCTACCCCGCCAGTTACGTACTTCCCTCACCGGTGTATTATC

CCCGTTCTCACTACTATCCCAGGTATCTTGTGAACCAGAAGGCTTTCAAA

GAAGATGACATGCAGACTGTGGATGACCAGGAGGAAATGAGTCCTGTTGC

GCCTCCTGCAGGGGAGCGAGATTTGTCTCACCGTCGCCACCACAGTCCCG

```
CCCCGTACGGCTATTATTACTCCCCCGCAGAATACTATACCCCAAAGCAC

TACGTGGGAAGTCCTTATCCCAGATATCTCAAAGAGGCACGGCGTGCGGC

AGTTGTCGATAAAAGTGCAGCGGCGCAGTCGAAGTTCATGGCTGCATCTA

GGAAAGTTAGGAACATGGGACATCGCCGGTATGGCTACTACCACGTCCCC

CTTCCTTACTACAGCTCTTACTACGGATACAGGAACTCGCCTTACGGTTA

TGTCCGCTATCTCTATTGA.
```

In certain embodiments, a TyRP3 polypeptide, e.g., as used to generate an antibody as described herein, may be recombinantly derived from the *T. gondii* M4 strain. In other instances, a TyRP3 polypeptide, e.g., as used to generate an antibody as described herein, may be recombinantly derived from the *T. gondii* ME49 strain.

In some instances, an antibody directed to a TyRP3 polypeptide specifically binds to an epitope of the TyRP3 polypeptide. In some instances, an antibody directed to a TyRP3 polypeptide specifically binds to a linear epitope of the TyRP3 polypeptide. In some instances, an antibody directed to a TyRP3 polypeptide specifically binds to a conformational epitope of the TyRP3 polypeptide. Determination of the particular epitope to which an anti-TyRP3 polypeptide binds may be determined empirically through epitope mapping performed by one or more techniques including but not limited to, e.g., x-ray crystallography, olio-peptide scanning (i.e. pepscan), site-directed mutagenesis, mutagenesis mapping, hydrogen-deuterium exchange, phage display, limited proteolysis, and the like.

In one embodiment, an antibody as described herein is derived from a recombinant polypeptide that shares at least 75% sequence identity with TyRP4 of SEQ ID NO:10. In one embodiment, an antibody as described herein is derived from a recombinant polypeptide that shares at least 80% sequence identity with TyRP4 of SEQ ID NO:10. In one embodiment, an antibody as described herein is derived from a recombinant polypeptide that shares at least 85% sequence identity with TyRP4 of SEQ ID NO:10. In one embodiment, an antibody as described herein is derived from a recombinant polypeptide that shares at least 90% sequence identity with TyRP4 SEQ ID NO:10. In one embodiment, an antibody as described herein is derived from a recombinant polypeptide that shares at least 95% sequence identity with TyRP4 of SEQ ID NO:10. In one embodiment, an antibody as described herein is derived from a recombinant polypeptide that shares 100% sequence identity with TyRP4 of SEQ ID NO:10. In one embodiment, an antibody as described herein is derived from a full length TyRP4 recombinant polypeptide of SEQ ID NO:10.

TyRP4, Amino Acid Sequence:

```
                                          (SEQ ID NO: 10)
MYFKMKVFNFVLLMAIIAASVSAAKAESEHVGDAKPLHKEIRAEQPSVVQ

EGLQQNRDNPTRELFPRLWGYGGYGYGYPYAGYSYGYYGYPYAGYTYYGY

PYGAYYGYGGYYW.
```

TyRP4 Nucleic Acid Coding Sequence:

```
                                          (SEQ ID NO: 11)
ATGTATTTTAAGATGAAGGTGTTCAACTTCGTTTTGCTCATGGCCATCAT

TGCCGCGTCTGTGTCGGCTGCCAAAGCGGAATCCGAACATGTTGGTGACG

CGAAGCCCTTGCACAAAGAAATCCGCGCCGAACAGCCATCGGTTGTGCAG

GAAGGACTTCAACAGAACAGAGATAATCCTACACGGGAGCTATTCCCCAG

ACTCTGGGGGTATGGAGGCTACGGTTACGGCTACCCCTACGCAGGGTACA

GCTACGGCTACTACGGCTACCCATATGCAGGATACACCTACTACGGCTAC

CCGTATGGTGCATACTATGGCTACGGTGGGTATTACTGGTAA.
```

The genomic locus of TyRP4 is provided below with the non-coding sequence (e.g., introns indicated as lower case:

```
                                          (SEQ ID NO: 12)
ataaatcatataatcacgtccgtcacacttcaatttgttacttcacgttc tgacttccgacagtctacgttaggtgcaacgacttcgtctaattccaaca tccaggaacaccaacgttctATGTATTTTAAGATGAAGGTGTTCAACTTC

GTTTTGCTCATGGCCATCATTGCCGCGTCTGTGTCGGCTGCCAAAGCGGA

ATCCgtaagcattaacgtaattggtcacctgcagggcaagcgtcttccag gaaatcgcctttgatatgcccgtcacacgtgtgtgtgattttcagGAAC

ATGTTGGTGACGCGAAGCCCTTGCACAAAGAAATCCGCGCCGAACAGCCA

TCGGTTGTGCAGGAAGGACTTCAACAGAACAGAGATAATCCTACACGGGA

GCTATTCCCCAGACTCTGGGGGTATGGAGGCTACGGTTACGGCTACCCCT

ACGCAGGGTACAGCTACGGCTACTACGGCTACCCATATGCAGGATACACC

TACTACGGCTACCCGTATGGTGCATACTATGGCTACGGTGGGTATTACTG

GTAActgtgcgaacaaaaattacagtcacgatcaaatctgttgtcatgcc tggaaccacagatacctgttggagcaggcagctactgatgcagatttcc agagtatggcttctgagaggatgacgatggggatggaattagctgaggga tcagggaaaagtgctccaagttcgtgtggccgcgccaaccgatgggaat ttttaacgacgaatatgtggttccatgttcgggtataatttgaacccggt tcacgaagaaacgtttttctaatctaaagttgttgtcgcagtaaacgacg tgtagggtctccgctgaattgactggcactctgcttggtcaagagcccct gtctagcctatacacagctaggaacgaacgtttgacatgcgcttcatcaa ccaaacatgtagactatcgcacagttaaagggcagtgctttaaaaaa.
```

In certain embodiments, a TyRP4 polypeptide, e.g., as used to generate an antibody as described herein, may be recombinantly derived from the *T. gondii* M4 strain. In other instances, a TyRP4 polypeptide, e.g., as used to generate an antibody as described herein, may be recombinantly derived from the *T. gondii* ME49 strain.

In some instances, an antibody directed to a TyRP4 polypeptide specifically binds to an epitope of the TyRP4 polypeptide. In some instances, an antibody directed to a TyRP4 polypeptide specifically binds to a linear epitope of the TyRP4 polypeptide. In some instances, an antibody directed to a TyRP4 polypeptide specifically binds to a conformational epitope of the TyRP4 polypeptide. Determination of the particular epitope to which an anti-TyRP4 polypeptide binds may be determined empirically through epitope mapping performed by one or more techniques including but not limited to, e.g., x-ray crystallography, olio-peptide scanning (i.e. pepscan), site-directed mutagenesis, mutagenesis mapping, hydrogen-deuterium exchange, phage display, limited proteolysis, and the like.

In one embodiment, an antibody as described herein is derived from a recombinant polypeptide that shares at least 75% sequence identity with TyRP5 of SEQ ID NO:13. In one embodiment, an antibody as described herein is derived from a recombinant polypeptide that shares at least 80% sequence identity with TyRP5 of SEQ ID NO:13. In one embodiment, an antibody as described herein is derived from a recombinant polypeptide that shares at least 85% sequence identity with TyRP5 of SEQ ID NO:13. In one embodiment, an antibody as described herein is derived from a recombinant polypeptide that shares at least 90% sequence identity with TyRP5 SEQ ID NO:13. In one embodiment, an antibody as described herein is derived from a recombinant polypeptide that shares at least 95% sequence identity with TyRP5 of SEQ ID NO:13. In one embodiment, an antibody as described herein is derived from a recombinant polypeptide that shares 100% sequence identity with TyRP5 of SEQ ID NO:13. In one embodiment, an antibody as described herein is derived from a full length TyRP5 recombinant polypeptide of SEQ ID NO:13.

TyRP5 Amino Acid Sequence:

(SEQ ID NO: 13)
MKLLTPLFLSGLVVAAAAQDGQEPPSELAEQIVSSLGPDDVEDGADDREL
GGKKSGGYIPAMPVKKTPVTKVTYLPTPKKAAQPIVYASSKKGDYLPRKL
QDIDTDETDAIRSDEELDTEESQTADESADDRELGGKKNRGGYIPVKLPP
PKKVVVAPKKVATPIYAGKKGYWGGGYYRRLGEEPDTEDELVEELEAEEP
EESQTADESADDRELGGKKNRGGYIPVKLPPPKKVVVAPKKVATPIYAGK
KGYWGGGYYRRLGEEPDTEDELVEELEAEEPEESQTADESADDRELGGKK
NRGGYIPVKLPPPKKVVVAPKKVATPIYAGKKGYWGGGYYRRLGEEPDTE
DELVVELEAEEPEESQTADESADDRELGGKKNRGGYIPVKLPPPKKVVVA
PKKVATPIYAGKKGYWGGGYYRRLGEEPDTEDELVEELEAEEPEELQAQE
PEESADEAADGRELGKSTYGGYSYSPSSKKTTVQPSYTTKVVRRPKKVDQ
PAPKKLIRSEPKKSVSYQPKKTVRTVSKKTVSPVPKKAVQAQPKKTLSYR
PVIEAQTKKSTHYAPHYTSKKGSY.

TyRP5 Nucleic Acid Coding Sequence:

(SEQ ID NO: 14)
ATGAAGCTCTTGACTCCCCTTTTTCTGTCCGGGCTTGTTGTGGCAGCGGC
AGCTCAAGACGGACAAGAGCCTCCCAGTGAGTTAGCGGAACAGATCGTTT
CTTCTCTTGGCCCGGACGATGTAGAGGATGGCGCTGACGATCGAGAGCTC
GGAGGTAAAAAATCGGGTGGCTATATTCCTGCTATGCCAGTGAAGAAGAC
ACCAGTAACCAAAGTGACCTATTTGCCCACTCCGAAGAAAGCAGCCCAGC
CAATTGTCTACGCATCATCCAAAAAAGGTGACTACCTACCACGCAAGCTC
CAAGACATCGATACAGACGAGACTGATGCCATCCGCTCCGACGAAGAACT
CGACACAGAGGAATCACAGACGGCCGACGAATCGGCCGATGATCGCGAAC
TCGGGGGCAAGAAGAATCGTGGTGGCTATATTCCTGTAAAGCTACCACCG
CCCAAAAAAGTTGTCGTTGCTCCCAAGAAGGTGGCCACTCCGATCTACGC
TGGCAAGAAAGGATACTGGGGCGGAGGCTACTACCGCCGCCTCGGTGAGG
AACCAGATACAGAAGACGAGCTCGTCGAGGAACTGGAGGCCGAAGAGCCC

GAGGAATCACAGACGGCCGACGAATCGGCCGATGATCGCGAACTCGGGGG
CAAGAAGAATCGTGGTGGCTATATTCCCGTAAAGCTACCACCGCCCAAAA
AAGTTGTCGTTGCTCCCAAGAAGGTGGCCACTCCGATCTACGCTGGCAAG
AAAGGATACTGGGGCGGAGGCTACTACCGCCGCCTCGGTGAGGAACCAGA
TACAGAAGACGAGCTCGTCGAGGAACTGGAGGCCGAAGAGCCCGAGGAAT
CACAGACGGCCGACGAATCGGCCGATGATCGCGAACTCGGGGGCAAGAAG
AATCGTGGTGGCTATATTCCTGTAAAGCTACCACCGCCCAAAAAAGTTGT
CGTTGCTCCCAAGAAGGTGGCCACTCCGATCTACGCTGGCAAGAAAGGAT
ACTGGGGCGGAGGCTACTACCGCCGCCTCGGTGAGGAACCAGATACAGAA
GACGAGCTCGTCGTTGAACTGGAGGCCGAAGAGCCCGAGGAATCACAGAC
GGCCGACGAATCGGCCGATGATCGCGAACTCGGGGGCAAGAAGAATCGTG
GTGGCTATATTCCTGTAAAGCTACCACCGCCCAAAAAAGTTGTCGTTGCT
CCCAAGAAGGTGGCCACTCCGATCTACGCTGGCAAGAAAGGATACTGGGG
CGGAGGCTACTACCGCCGCCTCGGTGAGGAACCAGATACAGAAGACGAGC
TCGTCGAGGAACTGGAGGCCGAAGAGCCCGAGGAATTACAGGCACAAGAG
CCCGAGGAGTCGGCAGATGAGGCTGCCGACGGCCGCGAACTCGGCAAAAG
CACGTACGGTGGCTACAGCTACTCTCCGTCCAGCAAAAAGACAACCGTAC
AGCCTTCCTACACCACTAAAGTTGTTCGACGCCCCAAAAAGGTTGACCAG
CCTGCGCCAAAGAAGCTCATTCGCTCCGAGCCCAAGAAAAGCGTTAGCTA
TCAGCCGAAGAAGACTGTACGTACAGTCTCTAAGAAAACTGTGAGTCCGG
TTCCGAAAAAGGCTGTTCAGGCGCAGCCGAAGAAGACCCTCAGTTACCGA
CCGGTAATTGAGGCGCAAACAAAGAAGAGCACGCACTACGCTCCTCATTA
TACTTCAAAGAAGGGATCGTACTAA.

In certain embodiments, a TyRP5 polypeptide, e.g., as used to generate an antibody as described herein, may be recombinantly derived from the T. gondii M4 strain. In other instances, a TyRP5 polypeptide, e.g., as used to generate an antibody as described herein, may be recombinantly derived from the T. gondii ME49 strain.

In some instances, an antibody directed to a TyRP5 polypeptide specifically binds to an epitope of the TyRP5 polypeptide. In some instances, an antibody directed to a TyRP5 polypeptide specifically binds to a linear epitope of the TyRP5 polypeptide. In some instances, an antibody directed to a TyRP5 polypeptide specifically binds to a conformational epitope of the TyRP5 polypeptide. Determination of the particular epitope to which an anti-TyRP5 polypeptide binds may be determined empirically through epitope mapping performed by one or more techniques including but not limited to, e.g., x-ray crystallography, olio-peptide scanning (i.e. pepscan), site-directed mutagenesis, mutagenesis mapping, hydrogen-deuterium exchange, phage display, limited proteolysis, and the like.

In some instances, a polypeptide from which an antibody of the instant disclosure is derived may be a recombinant mutant polypeptide. In one embodiment, a mutant polypeptide is a recombinant mutant relative to the wild-type amino acid sequence of Tg25. In one embodiment, a mutant polypeptide is a recombinant mutant relative to the wild-type amino acid sequence of TyRP1. In one embodiment, a mutant polypeptide is a recombinant mutant relative to the wild-type amino acid sequence of TyRP2. In one embodiment, a mutant polypeptide is a recombinant mutant relative to the wild-type amino acid sequence of TyRP3. In one embodiment, a mutant polypeptide is a recombinant mutant relative to the wild-type amino acid sequence of TyRP4. In one embodiment, a mutant polypeptide is a recombinant mutant relative to the wild-type amino acid sequence of TyRP5. Mutant *T. gondii* oocyst polypeptides may differ relative to a wild-type sequence in any manner including but not limited to, e.g., one or more substitution mutations, one or more insertion mutations, one or more deletion mutations, one or more truncation mutations, and combinations thereof.

In some instances, a mutant polypeptide of the instant disclosure may be essentially full length, e.g., relative to the wild-type amino acid sequence of the polypeptide, and have at least one amino acid substitution mutation. The number of substitution mutations in such mutant full length polypeptides will vary and in some instances may range from 1 to 20 or more, including but not limited to, e.g., 1 substitution, up to 2 amino acid substitutions, up to 3 amino acid substitutions, up to 4 amino acid substitutions, up to 5 amino acid substitutions, up to 6 amino acid substitutions, up to 7 amino acid substitutions, up to 8 amino acid substitutions, up to 9 amino acid substitutions, up to 10 amino acid substitutions, up to 11 amino acid substitutions, up to 12 amino acid substitutions, up to 13 amino acid substitutions, up to 14 amino acid substitutions, up to 15 amino acid substitutions, up to 16 amino acid substitutions, up to 17 amino acid substitutions, up to 18 amino acid substitutions, up to 19 amino acid substitutions, up to 20 amino acid substitutions, etc. The manner of introducing such amino acid substitutions, e.g., through mutation of an encoding nucleic acid, and corresponding encoding nucleic acids to mutated polypeptide will be readily apparent to one or ordinary skill in the art.

In certain embodiments, polypeptides useful as antigens in developing *T. gondii* antibodies may be produced by synthetic means, including but not limited to recombinant expression from cDNA, recombinant expression from synthetic DNA, in vitro synthesis, cell-free synthesis, chemical synthesis, and the like.

In some instances recombinant or synthetic polynucleotides may include additional heterologous or synthetic sequence that are, e.g., attached to the sequence of interest. Attached additional sequences may be directly attached or may be attached through the use of a polynucleotide linker. Additional sequences can be included, e.g., in the expression vector into which a polynucleotide sequence of interest is inserted. In some instances, additional sequence attached to a polynucleotide of interest or included in a vector into which a polynucleotide sequence of interest is inserted may include but is not limited to nucleic acid sequence encoding one or more signal peptides and/or polypeptide tags, e.g., His-tag (e.g., a poly histidine tag, e.g., hexa-histidine), MAT-Tag, FLAG tag, recognition sequence for enterokinase, honeybee melittin secretion signal, beta-galactosidase, glutathione S-transferase (GST) tag. Such tag or signal sequences may, in some instances, by adjacent to the sequence encoding for the *T. gondii* polypeptide of interest and facilitate in the secretion, identification, proper insertion, positive selection of recombinant virus, and/or purification of the recombinant protein. In some instances, a vector into which a sequence encoding a *T. gondii* oocyst of interest is inserted may also include or be configured to include a Kozak sequence. Methods of cloning such additional sequence in desired and operable orientation/linkage to sequence encoding a polypeptide of interest are well known to the skilled artisan.

In some instances, genes or polynucleotides or subunits thereof encoding for a *T. gondii* oocyst polypeptide or fragment thereof may be contained within an appropriate vector for expression in a eukaryotic expression system or a prokaryotic expression system. Appropriate vectors for expressing such polypeptides in a eukaryotic expression system and generating recombinant protein include but are not limited to baculovirus expression vectors. The term "baculovirus expression vector", as used herein may refer to either the genetic component or genome of a baculovirus, e.g., engineered for use in expressing a recombinant gene, or an entire baculovirus expression system containing a recombinant baculovirus genome and other viral components. Baculovirus expression vectors may differ from naturally occurring baculovirus, e.g., through the absence or mutation of one or more naturally occurring baculovirus gene. For example, in some instances, a naturally occurring baculovirus gene, e.g., a polyhedrin gene, may be replaced with a recombinant gene of interest, e.g., an *T. gondii* oocyst gene or *T. gondii* oocyst polypeptide, in order to allow for expression of the recombinant gene of interest by baculovirus from the baculovirus expression vector or altered baculovirus genome.

Many baculoviruses, including AcNPV, form large protein crystalline occlusions within the nucleus of infected cells. A single polypeptide, referred to as a polyhedrin, accounts for approximately 95% of the protein mass of these occlusion bodies. The gene for polyhedrin is present as a single copy in the AcNPV viral genome. Because the polyhedrin gene is not essential for virus replication in cultured cells, it can be readily modified to express foreign genes. The foreign gene sequence is inserted into the AcNPV gene just 3' to the polyhedrin promoter sequence such that it is under the transcriptional control of the polyhedrin promoter.

Baculoviruses are particularly well-suited for use as eukaryotic cloning and expression vectors. They are generally safe by virtue of their narrow host range which is restricted to arthropods. The U.S. Environmental Protection Agency (EPA) has approved the use of three baculovirus species for the control of insect pests. AcNPV has been applied to crops for many years under EPA Experimental Use Permits.

In some instances, polypeptides of the instant disclosure may be generated by recombinant synthesis from baculovirus, e.g., through replacement of a baculovirus gene with a gene derived from *T. gondii* or a synthetic polynucleotide having sequence similarity to a gene of *T. gondii*. Baculovirus particles may be produced from recombinant baculovirus expression vectors containing polynucleotides encoding a *T. gondii* oocyst polypeptide through any convenient method. Generally, recombinant baculovirus expression vectors, including but not limited to Bacmids or recombined baculovirus genomes, are transfected into host cells sufficient for the production of baculovirus particles containing the recombinant baculovirus expression vectors.

Systems, vectors, cells, and reagents for the production of recombinant transfer vectors, recombinant baculovirus expression vectors and baculovirus particles are commercially available and include but are not limited to, e.g., those available from Life Technologies, Inc. (Grand Island, N.Y.) (including e.g., the Bac-to-Bac® Baculovirus Expression System, the pFastBac™ vector, pFastBac™ TOPO®, Baculovirus Expression System with Gateway®, BaculoDirect™, etc.), those available from BD Biosciences (San Jose, Calif.) (including, e.g., AcNPV C6 Wild-type Baculovirus DNA, BaculoGold™ AcRP23.lacZ Baculovirus DNA, AcUW1.lacZ Baculovirus DNA, pAcGP67, pAcSECG2TA, pVL1392, pVL1393, pAcGHLT, pAcAB4, etc.), those available from Sigma-Aldrich (St. Louis, Mo.) (including, e.g., pPolh-FLAG™, pPolh-MAT™, etc.), Protein Sciences Corporation (Meriden, Conn.) (including, e.g., expresSF+ cells, etc.), those from EMD Millipore (Danvers, Mass.) (pBAC-3, pBAC-6, pBACgus-6, and pBACsurf-1, etc.) and the like.

Methods

Aspects of the instant disclosure include methods including but not limited to methods of making antibodies directed to *T. gondii* oocysts, methods of detecting *T. gondii* oocysts and methods of separating *T. gondii* oocysts from a sample. Such methods make use of the antibodies and polypeptides described herein and/or result in the production of the antibodies and polypeptides described herein.

Methods of Making

Aspects of the instant disclosure relate to methods of making antibodies that bind to the intact *T. gondii* oocyst wall derived from recombinant *T. gondii* oocyst wall proteins. Such antibodies may be derived through the production of one or more recombinant *T. gondii* oocyst wall polypeptides or mutants thereof, as described above, e.g., through expression of such polypeptides in a eukaryotic expression system or a prokaryotic expression system, or through other synthetic means.

In some instances, a recombinant *T. gondii* oocyst wall polypeptide used in making an antibody that binds to an intact *T. gondii* oocyst wall is a full-length recombinant polypeptide as compared to a corresponding *T. gondii* wild-type protein.

Methods useful in making *T. gondii* oocyst wall polypeptides, e.g., including making full-length *T. gondii* oocyst wall polypeptides, for use in generating *T. gondii* oocyst wall antibodies will vary and may, in some instances, include eukaryotic expression systems including but not limited to baculovirus-based expression systems.

In some instances, a baculovirus vector is recombinantly configured to express a *T. gondii* polypeptide, e.g., as described herein, and then the virus is amplified and, in some instances, may purified for infection of host cells in order to generate recombinant *T. gondii* polypeptide. Viral particles may be purified from the media using any known purification method such as, e.g., sucrose density gradient centrifugation, and may be stored, e.g., at −70° C. or used in infection of cells for protein production.

Suitable host cells for use in generating baculovirus particles or expressing recombinant proteins from a baculovirus expression vector generally include insect cells. Virus production and protein production may be performed in vivo or in vitro. In vitro production of baculovirus particles or recombinant proteins may be performed with insect cell culture lines including adherent and non-adherent insect cells.

Recombinant baculoviruses replicate in a variety of insect cells, including continuous cell lines derived from the fall armyworm, *Spodoptera frugiperda* (Lepidoptera; Noctuidae). *S. frugiperda* cells have a population doubling time of 18 to 24 hours and can be propagated in monolayer or in free suspension cultures. Recombinant proteins described herein can be produced in insect cells including, but not limited to, cells derived from the Lepidopteran species *S. frugiperda*. Other insect cells that can be infected by baculovirus, such as those from the species *Bombyx mori*, *Galleria mellanoma*, *Trichplusia ni*, or *Lamanthria dispar*, can also be used as a suitable substrate to produce recombinant proteins described herein. In certain embodiments the host cells used in the methods described herein include established insect cell lines including but not limited to, e.g., 519 cells, Sf21 cells, High FiveT cells, ExpressSF+ cells, and the like.

As mentioned above, host cells of the instant disclosure may be grown in suspension culture or monolayer culture. Accordingly, cells may be grown using any convenient and appropriate culture methods and in any convenient and appropriate culture vessel, including but not limited to, e.g., culture plates, culture flasks, spinner flasks, bioreactors, and the like.

Sf900+ and Sf9 cells may be propagated at 26-30° C., e.g., 28° C. without carbon dioxide supplementation. The culture medium used for Sf9 cells is generally TNMFH, a simple mixture of salts, vitamins, sugars and amino acids, supplemented with 10% fetal bovine serum. Serum free culture medium (available as Sf900 culture media, GIBCO® BRL, Gaithersburg, Md.) can also be used to grow Sf9 cells and for propagation of Sf900+ cells. Sf9 cells have a population doubling time of 18-24 hours and can be propagated in monolayer or in free suspension cultures.

In some instances, host cells may be cultured under conditions sufficient for the production of extracellular virus, non-occluded virus, or budded virus such that baculovirus particles may be released into the cell culture medium. Culture medium containing non-occluded baculovirus particles may be used to subsequently infect one or more additional cultures of host cells.

In some instances, host cells may be cultured under conditions sufficient for the production of occluded virus during the viral occlusion protein phase. A recombinant baculovirus expression vector may utilize a baculovirus promoter expressed during the viral occlusion protein phase to drive production of a heterologous protein from an introduced recombinant heterologous gene or genes, e.g., polynucleotide encoding for a *T. gondii* oocyst polypeptide.

Host cells, e.g., host cells containing recombinant *T. gondii* oocyst polypeptide, may be lysed by any convenient method including but not limited to, e.g., sonication, physical shearing, chemical lysis, and combinations thereof. Chemical lysis of cells may make use of any one or more convenient lysis enhancers in a lysis buffer. Useful lysis enhancers include but are not limited to detergents (e.g., Triton X-100, Triton X-114, NP-40, Brij-35, Brij-58, Tween 20, Tween 80, Octyl glucoside, Octyl thioglucoside, SDS, CHAPS, CHAPSO, etc.) and the like. Lysis buffer used in lysing host cells may include additional reagents that increase yield or increase the quality of the recombinant protein obtained following subsequent purification and isolation steps. Additional lysis buffer reagents may include but are not limited to protease inhibitors, phosphatase inhibitors, nucleases, etc.

Methods of purifying and/or isolating generated recombinant proteins, including, e.g., generated *T. gondii* oocyst polypeptides, include any convenient method for protein extraction and purification including methods for purifying tagged recombinant proteins. In some instances, methods of purifying and/or isolating generated recombinant proteins may include immobilized metal ion chromatography (IMAC) based purification methods, and the like. In some instances, multiple methods of purifying and/or isolating generated recombinant proteins may be performed, e.g., multiple methods of purification may be performed in series, including, e.g., multiple rounds of a single purification method or a series of multiple different methods including but not limited to, e.g., column based purification followed by dialysis based purification. Methods of purifying and/or isolating generated recombinant proteins that find use in the methods described herein are well known in the art and described in, e.g., Janson (2011) Protein Purification: Principles, High Resolution Methods, and Applications, John Wiley & Sons, Inc. Hoboken, N.J.; Burgess & Deutscher (2009) Guide to Protein Purification, Academic Press (Elsevier), San Diego, Calif.; the disclosures of which are incorporated herein in their entirety. Following the generation of a purified recombinant protein or fragment thereof, in some instances, the concentration and/or purity of the protein may be assessed using any convenient method for measuring protein concentration or determining protein purity, including but not limited to, e.g., SDS-PAGE, silver stain, HPLC, mass-spectrometry, and the like.

Aspects of the instant disclosure include generating antibodies from recombinant *T. gondii* polypeptides. Methods of generating antibodies, including but not limited to, e.g., immunizing host animals, monitoring host animals for a serological response, generating hybridomas, antibody purification, antibody evaluation (e.g., affinity testing, specificity testing, etc.), and the like, are well known in the art. In some instances, antibodies generated against recombinant *T. gondii* oocyst polypeptides are evaluated and shown to bind both the recombinant *T. gondii* oocyst polypeptide from which the antibody was generated as well as *T. gondii* oocysts.

Detecting *T. gondii*

Aspects of the present disclosure include the detection of *T. gondii* oocysts in a sample through the use of antibodies as described herein. Such samples may be liquid samples or may be solid samples or semi-solid samples. In some instances, e.g., when a sample is a solid sample or a semi-solid sample, a sample must be first diluted or dissolved in an appropriate solution. In some instances, an appropriate solution for the dissolving of a solid or semi-solid sample may be water. Liquid samples may be used directly or may be diluted or concentrated prior to *T. gondii* oocyst detection as described herein.

Samples upon which detection of *T. gondii* oocysts may be performed will vary and may include but are not limited to, e.g., environmental samples, food-based samples, diagnostic samples and the like.

In some instances, the methods described herein may be used to detect the presence or absence of *T. gondii* oocysts in an environmental sample. Environmental samples include but are not limited to samples obtained from natural, rural, or urban environments and may further include water samples, soil samples, and the like. In some instances, the methods described herein may find use in detecting *T. gondii* oocysts in soil samples which may include samples obtained from soil suspected of containing parasites, e.g., *T. gondii*, or samples of soil obtained at or near a body of water suspected of containing parasites, e.g., *T. gondii*.

In some instances, the methods described herein may be used to detect the presence or absence of *T. gondii* oocysts in an environmental water sample. Environmental water samples will vary and may include but are not limited to, e.g., water samples obtained from ponds, lakes, streams, rivers, groundwater, above ground reservoirs, below ground reservoirs, run-off, estuaries, marshes, oceans, and the like. In some instances, environmental water samples are obtained from the human environment and include water collected or processed through human intervention including but not limited to, e.g., sewage, wastewater, storm water, water treatment plant input, water treatment plant output, water contained in a water treatment plant or being treated in a water treatment plant, stored water, water contained in plumbing or other water delivery systems, and the like. Environmental water samples may also include samples obtained by sampling a water storage container or transport device including empty or storage containers or transport devices such that the sample may be obtained by flushing the device to obtain a sample or using any convenient sample collection method, e.g., of sampling a surface, including but not limited to a swab, wipe, etc.

In some instances, methods of the instant disclosure allow for the direct detection of *T. gondii* oocyst in an environmental water sample without processing of the environmental water sample in order to permeabilize any *T. gondii* oocysts that may be contained in the sample. Such environmental water samples may, in some instances, be referred to as samples that have not been pre-processed for *T. gondii* oocyst detection and include but are not limited to samples that have not been mechanically processed, e.g., through the use of sonication, high pressure, high heat, low temperature, or other physical method of disrupting the *T. gondii* oocyst wall, samples that have not been chemically processed, e.g., through the use of detergents, acid, base, or other chemical method or biological method, e.g., including enzymatic digestion, of disrupting the *T. gondii* oocyst wall. As will be readily apparent to the ordinary skilled artisan, such samples that have not been processed to disrupt the oocyst wall, may nonetheless include samples that have been routinely filtered, e.g., to remove or concentrate particulates and/or debris, concentrated, e.g., to remove particulates and/or debris or concentrate the sample for oocysts, flocculated, e.g., to remove particulates and/or debris and/or concentrate the sample for oocysts.

In some instances, the methods described herein may be used to detect the presence or absence of *T. gondii* oocysts in a food-based sample. As used herein "food based samples" refers to any consumable product intended for human or animal consumption, including solid food stuffs, semi-solid food stuffs, liquid food stuffs, drinking water, and the like. In some instances, a sample for the detection of *T. gondii* oocysts as described herein may include a food stuff intended for human consumption that is suspected to contain *T. gondii* oocysts. In some instances, a sample for the detection of *T. gondii* oocysts as described herein may include a food stuff intended for consumption by domesticated animals (i.e. pet food) or livestock (i.e. feed), including but not limited to mammals, e.g., dogs, cats, horses, cows, pigs, sheep, goats, rodents, etc., or avians (i.e. birds), including poultry and foul, that is suspected to contain *T. gondii* oocysts. In some instances, a food based sample may include a sample obtained from water or other liquid that has come into contact with food stuffs, including but not limited to, e.g., wash water, water used in watering crops, water used in the production of food stuffs, etc. Food stuffs from which a sample may be derived include but are not limited to, e.g., vegetable, fruit, meat, beverages, grains, and the like.

In some instances, the methods described herein may be used to detect the presence or absence of *T. gondii* oocysts in a diagnostic sample. As used herein a "diagnostic sample" includes biological samples and may refer to a biological sample obtained to diagnose a condition or disease of a human or non-human animal. In some instances, a diagnostic sample may include a bodily sample obtained from a subject including but not limited to tissue, e.g., including skin, blood, etc., and cells, e.g., including skin cells, blood cells, etc. In other instances, a diagnostic sample may include a specimen obtained from a subject including but not limited to blood, urine, feces, sweat, saliva, tears, hair, and the like. In some instances, a diagnostic sample may be used in the detection of *T. gondii* oocysts in order to diagnose a subject as having a *T. gondii* infection. In some instances, a diagnostic sample may be used in the detection of *T. gondii* oocysts in order to diagnose a human subject as having a *T. gondii* infection. In some instances, a diagnostic sample may be used in the detection of *T. gondii* oocysts in order to diagnose a non-human subject as having a *T. gondii* infection. In some instances, a diagnostic sample may be used in the detection of *T. gondii* oocysts in order to diagnose a domesticated animal, e.g., a cat, as having a *T. gondii* infection, including but not limited to e.g., the detection of *T. gondii* oocysts in a cat or testing a cat for a *T. gondii* oocyst infection by assaying feces collected from the cat for the presence of oocysts. In some instances, a diagnostic sample may be used in the detection of *T. gondii* oocysts in order to diagnose a wild animal, e.g., a sea otter, as having a *T. gondii* infection.

In some instances, a sample as described herein includes a sample suspected of containing one or more organisms that are closely related to *T. gondii* or known to contain one or more organisms that are closely related to *T. gondii*. The methods as described herein allow for the specific detection of *T. gondii* in such samples or the differentiation of *T. gondii* oocysts from related organisms in such samples. In certain embodiments, a sample may be a sample suspected of containing or known to contain *Hammondia* spp., *Eimeria* spp., *Isospora* spp., *Giardia* spp. or *Cryptosporidium* spp, or any combination thereof. In some instances, by virtue of its source, a particular sample may have a high probability of containing one or more organisms closely related to *T. gondii*. For example, a sample may be obtained from an organism wherein it is known that the organism has a high probability of being infected by one or more organisms closely related to *T. gondii*, e.g., a cat. In an alternative example, a sample may be obtained from an environmental source where contamination with one or more organisms related to *T. gondii* is predicted, expected or known.

In some instances, a sample as described herein includes a sample suspected of containing one or more other waterborne zoonotic pathogens, including but not limited to, e.g., one or more waterborne protozoan pathogens. Other waterborne zoonotic pathogens suspected to be present in a subject sample may be closely related to *T. gondii* or may be essentially unrelated to *T. gondii*. Non-limiting examples of other waterborne zoonotic pathogens include but are not limited to species of *neospora*, species of *sarcocystis*, species of *giardia*, etc., and, e.g., those described in Environmental Protection Agency Publication No. EPA 822-R-09-002 *REVIEW OF ZOONOTIC PATHOGENS IN AMBIENT WATERS* (2009), available online at water(dot)epa(dot)gov, and World Health Organization Publication *Waterborne Zoonoses: Identification, Causes and Control* edited by J. A. Cotruvo, et al. (2004), available online at www(dot)who(dot)int, the disclosures of which are incorporated herein in their entirety by reference.

Aspects of the instant disclosure include the detection of *T. gondii* oocysts, e.g., in any of the above described samples using antibodies as described herein. As such, any conventional method of detection of antibody-antigen binding may find use in detecting a binding interaction between an antibody of the instant disclosure and a *T. gondii* oocyst. Generally, detection of a *T. gondii* oocyst in a sample involves contacting the sample with a *T. gondii* oocyst antibody, as described herein, and performing one or more detection methods.

In some instances, the instant disclosure includes immunofluorescence detection of a *T. gondii* oocyst in a sample and may in some instances be referred to as an immunofluorescence assay (IFA) which may include a direct or an indirect IFA as appropriate. Generally, immunofluorescence detection of a *T. gondii* oocyst in a sample involves contacting the sample with a *T. gondii* oocyst antibody and detecting the binding of the antibody to the oocyst. Binding of a *T. gondii* oocyst antibody to a *T. gondii* oocyst can be performed by a variety of methods. In some instances, a *T. gondii* oocyst antibody is directly conjugated to a detectable label such that binding of the *T. gondii* oocyst antibody to the *T. gondii* oocyst allows an observer or automated device to identify a signal produced by the detectable label that conforms to parameters, e.g., size, shape, morphology, etc., that are characteristic of a *T. gondii* oocyst and thus allowing detection. In some instances, a *T. gondii* oocyst antibody may not be directly conjugated to a detectable agent and thus a *T. gondii* oocyst may be indirectly detected by one or more subsequent detection steps including but not limited to, contacting the antibody bound *T. gondii* oocyst with a detectable agent that allows for detection of the oocyst, e.g., a fluorescent secondary antibody or binding partner or a secondary antibody or binding partner that allows for a detection reaction (e.g., a chemical, enzymatic, etc.). In some instances, stringency of a binding reaction may be increased and thus stringency of the detection reaction may be increased through the use of one or more wash steps following contacting a sample with a *T. gondii* oocyst antibody.

In some instances, a detectable signal need not be observed by a human observer and may instead be detected by a detection device. Suitable detection devices are described herein and known in the art. For example, in one embodiment, a fluorescently labeled *T. gondii* oocyst antibody or a *T. gondii* oocyst antibody that is bound by a fluorescent detection reagent may be detected on a flow cytometer.

In some instances, the detected presence of a *T. gondii* oocyst antibody may be compared to a control binding reaction or detection reaction. The use of such control reactions is well known in the art and may include, e.g., positive and negative controls. In some instances, a negative control binding reaction may exclude, e.g., the *T. gondii* oocyst antibody from the binding reaction or an essential detection reagent. In some instances, a positive control may detect the presence of an antigen to which a *T. gondii* oocyst antibody was raised, e.g., through binding an element of the antigen, e.g., a recombinant element including but not limited to a label, tag, signal sequence, etc. In one embodiment, a positive control reaction includes binding of a His-tag present on a recombinant *T. gondii* oocyst antigen.

In some instances, detection of a *T. gondii* oocyst may make use of methods for the isolation of *T. gondii* oocysts, as described below. For example, methods of *T. gondii* oocyst isolation utilizing a *T. gondii* oocyst antibody as described herein may be used to extract or concentrate *T. gondii* oocysts from or in a sample for visual detection or device mediated detection. Visual detection of such isolated or concentrated *T. gondii* oocysts may include conventional light microscopic based detection of *T. gondii* oocysts, including but not limited to, e.g., bright-field microscopy, phase-contrast microscopy, DIC microscopy, fluorescent microscopy, and the like.

In some instances, device mediated detection may make use of the presence of an element of the extraction, isolation, or concentration method, e.g., including detecting the element that allowed for the extraction, isolation, or concentration, including but not limited to, e.g., detection of a bound substrate (e.g., a nanosphere, a microsphere, a bound magnetic bead, a bound charged particle, etc.). Any conventional detection device useful in detecting a detectable signal, as described herein, may find use in such methods including but not limited to, magnetic detection devices, charge detection devices, etc.

Isolating *T. gondii*

Aspects of the instant disclosure include methods of isolating, extracting, and/or concentrating *T. gondii* oocysts through use of a *T. gondii* oocyst antibody as described herein. Any conventional means for separating an analyte from a sample based on binding of the analyte by a specific antibody may be employed in the methods described herein. It will be recognized by the ordinary skilled artisan wherein the isolation, extraction and/or concentration techniques described may be employed on samples, such as those described above and wherein methods, such as those described above for the detection of *T. gondii* oocyst may be amended or configured for use in the isolation, extraction, or concentration methods described herein.

In some instances a *T. gondii* oocyst may be isolated, extracted and/or concentrated from or in a sample based on the binding of a detectable antibody to the *T. gondii* oocyst. In some instances, a *T. gondii* oocyst may be bound by a detectable antibody and *T. gondii* oocyst may be sorted based on such binding. Methods for sorting detectable particles, e.g., those bound by fluorescently labeled or fluorescently detectable antibodies, are well known in the art and include but are not limited to, e.g., fluorescence activated cell sorting (FACS).

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus. Fluorescence-activated cell sorting (FACS) is a specialized type of flow cytometry. FACS provides a method for sorting a heterogeneous mixture of biological cells into two or more containers, generally one cell at a time, based upon the specific light scattering and fluorescent characteristics of each cell. The flow cytometer and the FACS machine are useful scientific instruments as they provide fast, objective and quantitative recording of signals, e.g., fluorescent signals, and/or detection of cellular characteristics, e.g., size, granularity, viability, etc., from individual cells as well as physical separation of cells of particular interest. Fluorescent signals used in flow cytometry, for instance when detecting or sorting labeled *T. gondii* oocysts, typically are fluorescently-tagged antibody preparations or fluorescently-tagged ligands for binding to antibodies or other antigen-, epitope- or ligand-specific agent, such as with biotin/avidin binding systems or fluorescently-labeled and optionally addressable beads (e.g. microspheres or microbeads).

In certain instances, flow cytometry is performed using a detection reagent, e.g., a fluorochrome-labeled antibody, e.g., a monoclonal antibody, with specific avidity against a *T. gondii* oocyst antigen. A sample is contacted with a detection reagent under conditions sufficient to allow the detection reagent to bind the *T. gondii* oocyst and the sample is loaded into the flow cytometer. The samples loaded into the flow cytometer are run through the flow cytometer, e.g., by flowing liquid sample through the flow cell of the flow cytometer. The flow cytometer detects events as the labeled *T. gondii* oocyst passes one or more detection areas of the flow cytometer. For example, the flow cytometer may detect fluorescence emitted from a fluorochrome of a detection reagent upon excitation of the fluorochrome with a particular wavelength of light. In some instances, the flow cytometer detects the relative intensity of a particular signal, e.g., fluorescence of a particular detection reagent, to quantify the level of the detectable agent present on the surface of the oocyte and/or to qualitatively categorize an analyte, e.g., as an analyte that is positive for a particular marker or an analyte that is negative for a particular marker. Detected events are counted or otherwise evaluated by the flow cytometer with or without input from an operator and used to determine, e.g., the total number of oocytes present in a sample. In instances where FACS is utilized oocytes may be sorted, e.g., into separate containers, based on the detection or measurement of a particular bound antibody. In some instances, FACS may be utilized to generate a concentrated sample of *T. gondii* oocysts or isolated *T. gondii* oocysts.

In some instances, conventional immunomagnetic separation techniques, e.g., those developed for the isolation and detection of *cryptosporidium* and described in Ochiai et al. Appl Environ Microbiol. 2005 February; 71(2):898-903; Sturbaum et al., Appl Environ Microbiol. 2002 June; 68(6): 2991-6; Yakub et al., Appl Environ Microbiol. 2000 August; 66(8):3628-31; Di Giovanni et al., Appl Environ Microbiol. 1999 August; 65(8):3427-32; Pereira et al., Appl Environ Microbiol. 1999 July; 65(7):3236-9; the disclosures of which are incorporated by reference herein in their entirety, may be adapted for use with *T. gondii* through the use of one or more of the antibodies described herein.

In some instances a *T. gondii* oocyst may be isolated, extracted and/or concentrated from or in a sample based on the binding of an antibody to the *T. gondii* oocyst bound to a magnetic particle, e.g., a magnetic bead. Methods for isolating and/or sorting magnetic particles, e.g., those magnetic particles bound to antibodies, are well known in the art and include but are not limited to, e.g., immunomagnetic separation (IMS).

IMS as it refers to the detection and isolation of parasites generally involves antibodies against parasite surface antigens bound to magnetic particles to capture and remove the parasite from the sample using a magnet. A critical feature in the success of IMS is the affinity and specificity of the antibody to the surface antigen of the parasite. Antibodies of the instant disclosure may be coupled to magnetic beads according to any convenient method including but not limited to, e.g., covalent linkages, biotin-avidin interactions, and the like. Any convenient magnetic substrate appropriate for use in IMS may find use in the subject methods, including but not limited to, e.g., magnetic beads, paramagnetic beads, super-paramagnetic beads, etc., provided the substrate is suitable or configured for binding or attachment to an antibody.

Magnetic beads may be attached to an antibody of the instant disclosure through binding of the antibody to a capture agent present on the surface of the bead. Attachment of antibodies to beads using a capture agent may be achieved through the use of any appropriate method, including but not limited to, e.g., conjugation, coating, coupling, etc., and those resulting in covalent attachment, e.g., through covalent binding of primary amine (NH2) groups, sulphydryl (SH) groups, etc., including but not limited to e.g., tosylactivated binding (i.e. p-toluene-sulfonyl mediated binding), carbodiimide mediated binding, epoxy mediated binding, and the like. In some instances, commercially available magnetic beads and/or kits that provide magnetic beads and reagents ready for attachment to an antibody of interest may be utilized in the methods as described herein including e.g., those available from Life Technologies (Grand Island, N.Y.), Merck Millipore (Billerica, Mass.), and the like.

In some instances, IMS may be performed using antibodies as described herein to achieve a particular percent recovery of *T. gondii* oocysts from a sample. For example, IMS may be performed using an antibody as described herein to achieve better than 40% recovery of *T. gondii* oocysts from a sample including but not limited to, e.g., better than 45% recovery, better than 50% recovery, better than 55% recovery, better than 60% recovery, better than 65% recovery, better than 68% recovery, etc.

In some instances, those methods described above for *T. gondii* oocyst detection and isolation may be combined in whole or in part. For example, in some instances a particular method may include isolation of *T. gondii* oocysts based on antibody binding, e.g., through the use of IMS, and isolated *T. gondii* oocysts may be subsequently detected based on antibody binding, e.g., through the use of a fluorescently detectable antibody. Any combination of the above methods and reagents may find use in particular isolation and/or detection methods.

Also provided are reagents, devices and kits thereof for practicing one or more of the above-described methods. The subject reagents, devices and kits thereof may vary greatly. Aspects of the present disclosure include kits and devices for the detection and/or isolation of *T. gondii* oocysts based on the binding of an antibody as described herein to intact *T. gondii* oocysts. Subject kits may include an antibody or pre-conjugated antibody as described herein and, optionally, one or more additional reagents for the use of such an antibody in the methods as described herein. Such additional reagents may include but are not limited to additional detection reagents, control reagents (e.g., antigen polypeptides, control beads, calibration reagents, etc.), buffers (e.g., wash buffers, running buffers, etc.) and the like.

The antibodies, detectable labels and/or reagents described above may be provided in liquid or dry (e.g., lyophilized) form. Any of the above components (detectable labels and/or reagents) may be present in separate containers (e.g., separate tubes, bottles, or wells in a multi-well strip or plate). In addition, one or more components may be combined into a single container, e.g., a glass or plastic vial, tube or bottle.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, removable drive, flash drive, etc., on which the information has been recorded. Yet another means that may be present is a website address which may be used via the internet to access the information at a removed site. Any convenient means may be present in the kits.

Subject devices may include an antibody or pre-conjugated antibody as described herein and, optionally, one or more additional reagents for use of such an antibody in the methods as described herein. Alternatively, subject devices may include an antibody and one or more reagents for conjugating to the antibody including but not limited to, e.g., a detectable label, a magnetic bead, etc., to be used prior to using the device according to the methods described herein. Such devices may include but are not limited to immunological detection devices such as immuno-based "dipstick" devices, lateral flow immuno-assay devices, ELISA-based devices, and the like. Configuration of such devices and how such configurations may be adapted for use with the antibodies and methods as described herein will be readily apparent to those of skill in the art upon review of the instant disclosure. In some instances, such devices may be specifically configured for use in water monitoring. In some instances, kits for practicing the subject methods may include such devices as a component of the kit.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Materials and Methods

Parasite Strain:

The M4 strain isolated from an infected sheep in Scotland kindly provided by Lee Innes of the Moredun Institute was used in these studies. Based on its European origin and the fact that, at each of 4 polymorphic loci, the M4 strain was found to have a DNA sequence identical to that of the canonical Type II ME49 strain (see, e.g., Fritz et al. (2012) PLoS One 7: e29998, the disclosure of which is incorporated herein by reference) M4 is believed to be a type II strain.

Oocyst Production:

Oocysts were produced in two kittens using routine methods (see, e.g., Fritz et al. (2012) J Microbiol Methods 88: 47-52, the disclosure of which is incorporated herein by reference). Briefly, outbred Swiss Webster mice were inoculated with previously generated oocysts. Mice were monitored serologically every two weeks for evidence of *T. gondii* infection beginning 3 weeks post-inoculation. At 8 weeks post-inoculation a small subset of mice were euthanized and examined for rate of infection. At 10 weeks, the remaining mice were euthanized and their brains fed to two kittens. Fecal flotations were performed on all fecal samples throughout the duration of kitten use for the project. Once kittens began to shed oocysts, oocysts were harvested from feces daily until shedding rates were markedly diminished. Oocysts were used for filtration experiments, to evaluate mAbs, and for IMS/DFA experiments.

Monoclonal Antibody Production

Antigen Target Selection:

Candidate oocyst wall genes were selected using analysis of the composition of *T. gondii* oocysts and the oocyst wall, target analytes for antibody development were selected that were present and abundant in oocyst walls.

A targeted approach to generate a strong and specific antibody response to selected proteins by immunizing mice with recombinant versions of the proteins was employed. Proteins that were predicted to be present in the oocyst wall met the following criteria: enriched in the oocyst wall fraction by mass spectrometry; contained a signal sequence (indicating the protein secretion and incorporation into the wall); and had homology to proteins of other stages and systems (e.g., homology to oocyst wall proteins in *Cryptosporidium parvum*) or had an amino acid composition indicative of cross-linking (e.g., tyrosine-rich).

Recombinant Expression of Protein:

Target genes/proteins were amplified and DNA sequenced. Predicted gene sequences were obtained from the *T. gondii* genome database (www(dot)ToxoDB(dot)org). Genes were PCR-amplified using designed gene-specific primers. Amplified DNA products were sequenced by the UC Davis Sequencing facility. Sequence analysis and contig assembly were performed in the laboratory using Invitrogen Vector NTI software. Each amplified gene was cloned into a TOPO-TA (Invitrogen) system according to manufacturer's instructions before extension sequences were added. When extension sequences were added (containing a Kozak sequence, signal peptide sequence, a 6×His tag and restriction sites for insertion into plasmid), products were cloned into a shuttle vector pFastBac1, for Bac-to-Bac Baculovirus Expression (Invitrogen). The pFasBac+toxo_gene_of_interest bacmid was then transformed into DH10Bac competent cells (Invitrogen). DH10 colonies containing the recombinant bacmid were grown on selective agar plates and screened by PCR for correct insertion of bacmid. DH10 colonies with desired insertion were expanded in culture and the recombinant bacmid DNA was isolated by ethanol precipitation. All primers used to amplify genes and generate bacmids are listed below in the descriptions of the corresponding amplification reactions.

Amplification Reactions:

PCR Amplification of TGME49_209610 (Tg25). Tg25 has 3 exons, so a total of 5 PCRs were done to stitch together the ORF (eliminate non-coding intron sequence) from M4 tachyzoite DNA. The reactions include:

The amplification of Exon 1 using tachyzoite DNA as template and primers

Tg25_Exon1_F
(ATGCCGACTATCTGTTCAAAGATCATTTGTGC, SEQ ID NO: 15)
and

Tg25_Exon1_Linker_R
(CCTCCAGAACACCAGATTGGCAGATAGCCTCTGGCTGTCCTGCAGCCTC

CTTC, SEQ ID NO: 16)

which produced an approximately 250 bp amplicon;

The amplification of Exon 2 using tachyzoite DNA as template and primers

Tg25_Exon2_Linker_F
(GAAGGAGGCTGCAGGACAGCCAGAGGCTATCTGCCAATCTGGTGTTCTG

GAGG, SEQ ID NO: 17)
and

Tg25_Exon2_Linker_R
(GTCTAACGCAATTTCCGTTGATCAATTGACCCTCTTTGCAGATGAATT

CCGGCTCTGATAAA, SEQ ID NO: 18)

which produced an approximately 1100 bp amplicon;

The amplification of Exon 3 using tachyzoite DNA as template and primers

Tg25_Exon3_Linker_F
(TTTATCAGAGCCGGAATTCATCTGCAAAGAGGGTCAATTGATCAACGGA

AATTGCGTTAGAC, SEQ ID NO: 19)
and

Tg25_Exon3_R
(CGCTTCGCACAACTCAACTGTGTATGACA, SEQ ID NO: 20)

which produced an approximately 70 bp amplicon;

The stitching of Exon 1 and 2 using the product of the amplifications of Exons 1 and 2 as template and primers Tg25_Exon1_F and Tg25_Exon2_Linker_R which produced an approximately 1300 bp amplicon;

The stitching of Exons 1, 2 and 3 using the product of the reaction used to stitch Exons 1 and 2 and the product of the amplification of Exon 3 as template and primers Tg25_Exon2_Linker_F and Tg25_Exon3_R which produced a 1389 bp amplicon. The final stitching product represents the complete ORF from start codon to stop codon.

PCR Amplification of TGME49_237080 (TyRP1). TyRP1 has only one exon and was amplified using M4 tachyzoite DNA as template and primers 037080_1F
(CCAGAACGAGGCTGCCAACTGTACT, SEQ ID NO: 21)
and

037080_4R
(CTGCAAGTAGGTCTTAATGGAAAGAAGTATGG, SEQ ID NO: 22)

which produced a 1456 bp amplicon which comprises the 1167 bp 037080 ORF and 5' and 3' UTR flanking sequence.

Extension sequences for insertion into the expression vector were performed. Addition of extension sequences for insertion into expression vector for TGME49_209610 (Tg25) were performed using the amplified gene product from above as template. The procedure involved a first amplification using the Ext1F+ExtR primers and a second amplification using the produced amplicon as a template and Ext2F+ExtR primers. The primers are as follows:

Tg25_Ext1F
(CCTGATGTTCATCGCTTTCGTCATCATCGCTGAGGCCCACGTTCCGGGA

ATGCCTGC, SEQ ID NO: 23),

Tg25_ExtR
(AGTCATCGACACTAGTTTAATGGTGGTGATGGTGATGTCCACCTGAACC

TCCCGCTTCGCACAACTCAACTGTGTATG, SEQ ID NO: 24),
and

TGall_Ext2F
(CTGATAAGTTACGGACCGAGCCGCCACCATGTACAAGCTCACAGTCTTC

CTGATGTTCATCGCTTTCGTCATC, SEQ ID NO: 25).

Addition of extension sequences for insertion into expression vector for TGME49_237080 (TyRP1) were performed using the amplified gene product from above as template. The procedure involved a first amplification using the Ext1F+ExtR primers and a second amplification using the produced amplicon as a template and Ext2F+ExtR primers. The primers are as follows:

037080_Ext1F
(CCTGATGTTCATCGCTTTCGTCATCATCGCTGAGGCCGAGGAAATGAGC

AGCGAAATGGTTG, SEQ ID NO: 26),

-continued

037080_ExtR
(AGTCATCGACACTAGTTTAATGGTGGTGATGGTGATGTCCACCTGAACC

TCCGTAGCACGCACCACCGGTGCT, SEQ ID NO: 27,
and

TGal1_Ext2F
(CTGATAAGTTACGGACCGAGCCGCCACCATGTACAAGCTCACAGTCTTC

CTGATGTTCATCGCTTTCGTCATC, SEQ ID NO: 28).

Expression and Purification of Recombinant Proteins:

Proteins were individually expressed using the Baculovirus Expression System (Invitrogen) as described by the manufacturer. Purified recombinant bacmid DNA was used for transfections into *Spodoptera frugiperda* cells (519). Viruses were rescued and propagated in Sf9 cells. Hexa-histidine tags engineered at the C-terminus of the recombinant proteins were utilized to purify the recombinantly expressed proteins by immobilized metal ion chromatography (IMAC) using HisPur Nickel NTA (Pierce). Proteins were buffer exchanged into PBS utilizing snake skin dialysis (ThermoScientific). Protein purity was assessed by SDS-PAGE and silver stain. Protein concentrations were then determined using a BCA protein quantification kit (Pierce).

Mouse Immunizations and Screening:

Mice were immunized and monitored serologically for immune response. For each recombinant protein produced, a group of eight 6-8 week old seronegative BALB-c mice were immunized. Each mouse received 75 µg of purified protein in 100 µl PBS mixed 1:1 with Titer Max Gold adjuvant, subcutaneously (SQ). Mice were boosted at 4-5-week intervals. Mice were monitored serologically for immune response by ELISA, either by using purified homologous recombinant protein as capture antigen or by In-Cell ELISA (recombinant proteins expressed in Sf9 cells in 96-well format and fixed for routine ELISA). Mice were evaluated every two weeks after the second immunization, using homologous recombinant protein as above, by Western Blot (against recombinant protein) and by IFA to *T. gondii* oocysts. Once a sufficiently high titer was observed in mice that had antibody responses to both the recombinant and native oocyst wall protein, a final immune challenge was performed: three weeks after the last boost 75 µg of recombinant protein in 100 µl PBS was administered intra-peritoneally (IP) 5 days pre-spleen harvest and 75 µg recombinant protein was administered intravenously (IV) 4 days pre-spleen harvest.

Hybridoma Production:

Monoclonal antibodies were developed and characterized. Mice that demonstrated the strongest immune responses were sacrificed and their spleen cells harvested for hybridoma formation. Monoclonal antibody production followed standard methodology for spleen cell/myeloma fusion using the ClonaCell-HY Hybridoma Kit (Stemcell Technologies). Hybridomas were initially screened by testing supernatant for reactivity to homologous recombinant protein by In-Cell ELISA and then to intact oocysts by IFA. For all reactive hybridomas, antibody isotype was determined using an isotyping kit (Pierce). Hybridoma clones producing high concentrations of antibody that detected both the homologous recombinant protein and intact *T. gondii* oocysts were expanded in culture for large-scale mAb purification. Monoclonal IgG antibodies were purified using recombinant Protein G—Sepharose 4B (Invitrogen). Recovered monoclonal antibodies were buffer-exchanged into PBS as above, concentrated by amicon filtration and quantified by BCA. Monoclonal IgM (anti-TyRP1) was purified by a variety of methods. Hybridoma supernatant for TyRP1 had excellent and specific reactivity with *T. gondii* oocysts, demonstrating that these antibodies are useful for both concentration by IMS or detection (IFA) of *T. gondii* oocysts. Two hybridomas were carried forward for mAb production for IMS/IFA experiments, one that binds to the protein product of TGME49_209610, designated Tg25.22 (IgG2b), and another that binds to the protein product of TGME49_237080, designated TyRP1.13 (IgM).

Antibody Specificity:

The specificity of the mAbs Tg25.22 and TyRP1.13 was evaluated by testing our antibodies against the oocysts/cysts of closely related organisms (*Eimeria, Isospora, Cryptosporidium, Giardia*, and *Hammondia* spp.) using an immunofluorescence assay. The tested antibodies did not react with any of the other organisms.

Figure 2A:
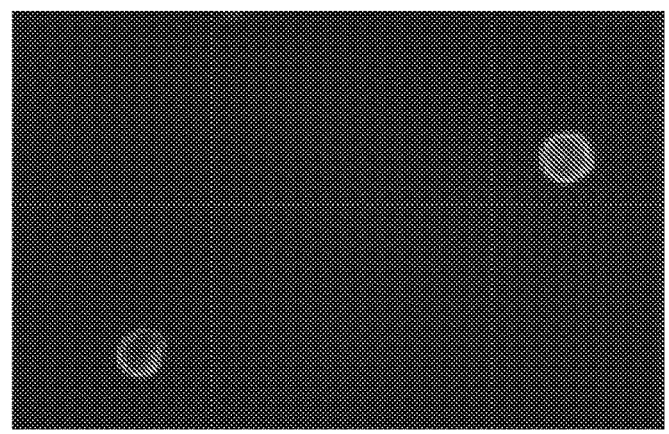
FIGS. 2A-B depict (A) the intact *T. gondii* oocyst wall labeled with monoclonal antibody and (B) the sporocysts of the labeled *T. gondii* oocyst shown by autofluorescence under UV excitation.
Figure 2B:
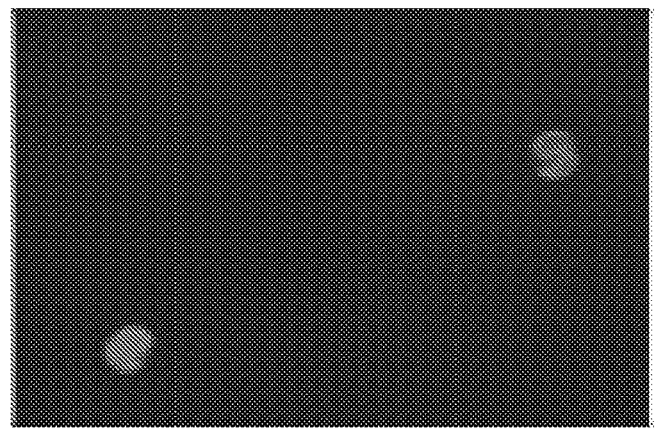

Development of *Toxoplasma gondii* Oocyst IMS Protocol for Water Testing:

Monoclonal antibodies were coupled to paramagnetic beads and the IMS sensitivity was evaluated in small-scale water testing. Monoclonal antibodies were coupled to paramagnetic beads according to manufacturer's instructions (Dynabeads, LifeTechnologies). Different types of beads were evaluated, including tosyl-activated and epoxy. The analytic sensitivity of the IMS system was evaluated through small-scale (1.5 or 5 mL water) laboratory spiking experiments using tap water. This procedure did not require a pre-concentration step. Water was spiked in triplicate with known numbers of *T. gondii* oocysts: 1000, 100, 10 and 0 oocysts. IMS was performed following routine protocols. The percent retention of oocysts by beads and also the percent recovery of oocysts by IMS were calculated.

To evaluate the binding efficiency of the antibody-coupled beads, the percent retention of oocysts by the antibody-coupled magnetic beads was calculated as "percent retention"=(total # oocysts in spike−# oocysts not bound by beads)/100. To do this, the number of oocysts not bound by beads was counted following incubation of oocysts with mAb-coupled beads. The unbound oocysts remained in the supernatant when beads were captured on the magnet. The number of unbound oocysts were counted by membrane filtration.

The percent recovery of oocysts by IMS was also determined. The percent recovery by IMS is expected to differ slightly from the percent retention because some oocysts are likely to be lost in bead washing steps and also to remain bound to the beads in the elution step. Oocysts were counted in all suspensions (primary suspension incubated with beads, all washes, the final eluate and oocysts that were still bound to beads following elutions) to determine where oocysts were lost in the procedure. IMS experiments were carried out with Tg25.22.

Immunofluorescent Detection of Oocysts:

*T. gondii* oocysts are autofluorescent under UV excitation, in the 330-385 nm range (corresponding to the DAPI filter used in conventional fluorescent microscopy). FIG. 1 shows autofluorescent oocysts. Oocysts shed in cat feces are unsporulated and initially non-infective. The top center oocyst in FIG. 1 is unsporulated. In the environment, oocysts sporulate within 24-72 hours to become infective. The bottom two oocysts in FIG. 1 are sporulated and the walls of the two sporocysts within the sporulated oocyst are also autofluorescent.

FIGS. 2A-B demonstrate *Toxoplasma gondii* oocysts labeled with the developed monoclonal antibodies detected by immunofluorescence. Oocysts in FIG. 2B are autofluorescent in the DAPI channel and appear blue. Oocysts in FIG. 2A that appear red in Texas Red channel are labeled with oocyst-wall-protein monoclonal antibodies (mAb), and a secondary Ab with a red fluorescent dye. All hybridoma supernatants that contained antibodies to the oocyst wall protein of interest, based on In-Cell ELISA screening as described above, were further evaluated for binding to oocysts. FIGS. 2A-B demonstrate strong binding of Tg25.22 to *T. gondii* oocysts.

Figure 3:
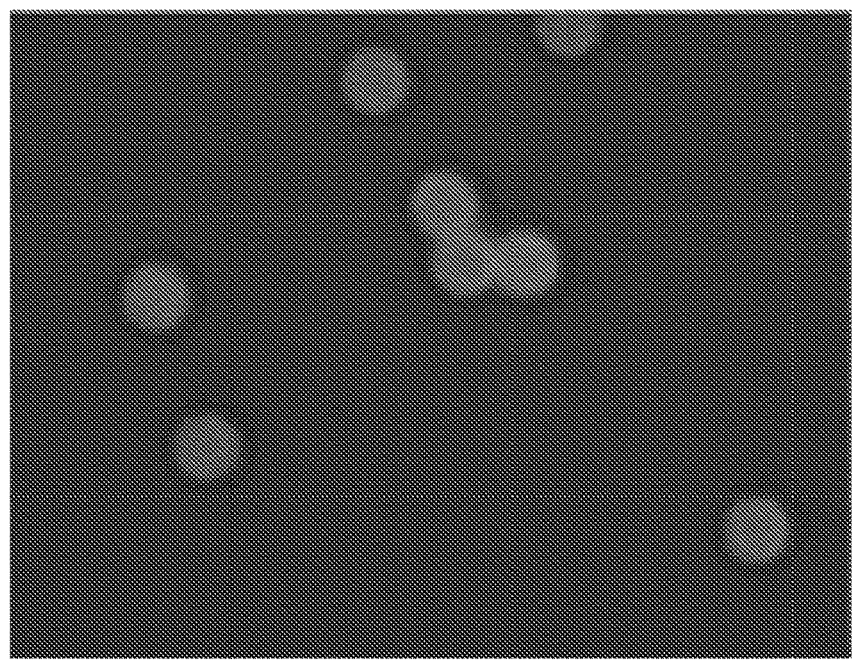
FIG. 3 depicts paramagnetic beads coupled with *T. gondii* monoclonal antibody imaged by contacting beads to a fluorescent secondary antibody.

Coupling of mAbs to Paramagnetic Beads and Binding of Oocysts:

FIG. 3 demonstrates paramagnetic beads coupled with mAb. For immunomagnetic separation (IMS) experiments, mAbs were coupled to paramagnetic beads. To confirm antibody coupling to beads, coupled beads were exposed to a secondary (goat-anti-mouse) antibody with FITC label (green) and imaged by fluorescent microscopy.

Figure 4:
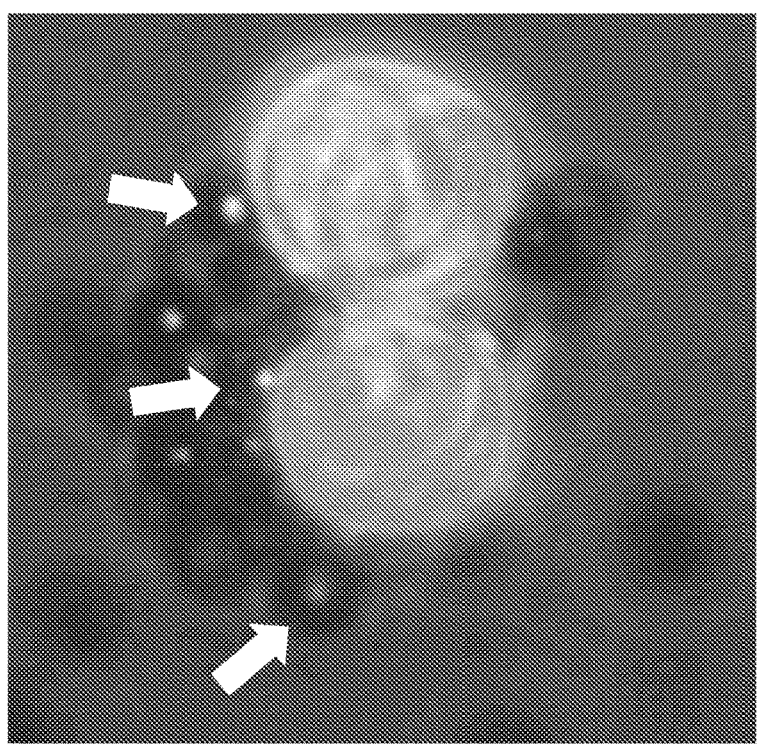
FIG. 4 depicts *T. gondii* oocysts bound to monoclonal antibody-coupled paramagnetic beads (arrows).
Figure 5:
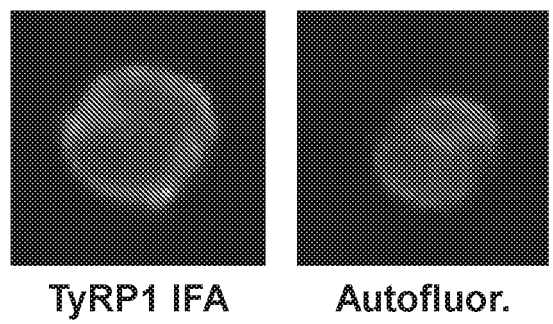
FIG. 5 depicts immunofluorescence of *T. gondii* oocyst wall labeled using serum from TyRP1 immunized mice (TyRP1) and autofluorescence under UV excitation, provided for reference, of sporocysts within the labeled intact *T. gondii* oocyst (Autofluor.).

FIG. 4 demonstrates the binding of paramagnetic bead coupled-mAb to *Toxoplasma* oocysts. Using paramagnetic beads coupled with *T. gondii* oocyst-specific mAb, IMS was performed on spiked water samples. In the IMS procedure the water sample (containing oocysts) was incubated with the beads (0.5 mg beads were added to 1 mL oocyst suspension) at 37° C. for 1 hour, with gentle rotation. The mAbs on the surface of the beads bound to the oocysts. The beads were then retained against a magnet and any material that is not bound to the beads was washed away. FIG. 4 shows several paramagnetic beads bound to one sporulated oocyst. Oocysts were eluted off of the beads using an acid solution (0.1 N hydrochloric acid) and the eluate is immediately neutralized with sodium hydroxide. Eluted oocysts were enumerated by epifluorescent microscopy.

Oocyst Recovery by IMS:

Sixty eight percent (68%) recovery was achieved in IMS experiments. Different bead types were explored for these experiments, including tosyl-activated beads and epoxy beads (Invitrogen). Tosyl-activated beads resulted in higher recoveries of *T. gondii* oocysts.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of specifically detecting an intact *Toxoplasma gondii* oocyst in a sample, the method comprising:
   a) contacting a sample suspected of containing a *T. gondii* oocyst with an IgG monoclonal antibody that specifically binds a protein on the outer wall of an intact *T. gondii* oocyst under conditions sufficient to form an immunocomplex of the antibody with the intact *T. gondii* oocyst; and
   b) specifically detecting the presence or absence of the immunocomplex comprising the antibody.

2. The method according to claim 1, wherein the sample has not been chemically pre-processed, mechanically pre-processed or both chemically and mechanically pre-processed to disrupt the *T. gondii* oocyst.

3. The method according to claim 1, wherein the sample is further suspected of containing an oocyst or cyst of an organism related to *T. gondii* selected from the group consisting of: *Hammondia* spp., *Eimeria* spp., *Isospora* spp., *Giardia* spp. and *Cryptosporidium* spp.

4. The method according to claim 1, wherein the antibody is detectably labeled.

5. The method according to claim 1, wherein the antibody is attached to a support.

6. The method according to claim 5, wherein the support is a bead comprising a surface bound capture agent, and the antibody is attached to the support by binding to the capture agent.

7. The method according to claim 1, wherein the protein is selected from the group consisting of TyRP1, TyRP2, TyRP3, TyRP4, TyRP5 and TgOWP2.

8. A method of specifically isolating an intact *Toxoplasma gondii* oocyst in a sample, the method comprising:
   a) contacting a sample suspected of containing a *T. gondii* oocyst with an IgG monoclonal antibody that specifically binds a protein on the outer wall of an intact *T. gondii* oocyst under conditions sufficient to form an immunocomplex of the antibody with the intact *T. gondii* oocyst; and
   b) specifically isolating the oocyst based on the binding of the antibody to the intact *T. gondii* oocyst.

9. The method according to claim 8, wherein the sample is further suspected of containing an oocyst or cyst of an organism related to *T. gondii* selected from the group consisting of: *Hammondia* spp., *Eimeria* spp., *Isospora* spp., *Giardia* spp. and *Cryptosporidium* spp.

10. The method according to claim 8, wherein the antibody is attached to a support.

11. The method according to claim 10, wherein the support is a bead comprising a surface bound capture agent, and the antibody is attached to the support by binding to the capture agent.

12. The method according to claim 8, wherein the protein is selected from the group consisting of TyRP1, TyRP2, TyRP3, TyRP4, TyRP5 and TgOWP2.

* * * * *

SEQUENCE LISTING

```
<160> NUMBER OF SEQ ID NOS: 28

<210> SEQ ID NO 1
<211> LENGTH: 462
<212> TYPE: PRT
<213> ORGANISM: Toxoplasma gondii

<400> SEQUENCE: 1

Met Pro Thr Ile Cys Ser Lys Ile Ile Cys Ala Leu Ser Val Leu Leu
1               5                   10                  15

Ala Thr Thr Ala His Val Pro Gly Met Pro Ala Leu Ala Ser Thr Asp
            20                  25                  30

Ala Thr Ile Met Lys Lys Ala Pro Gly Thr Tyr Pro Ala Pro Pro Pro
        35                  40                  45

Asp Pro Thr Arg Ala Arg Cys Lys Cys Pro Phe Gly Phe Glu Lys Met
    50                  55                  60

Asp Lys Ser Cys Val Lys Lys Glu Ala Ala Gly Gln Pro Glu Ala Ile
65                  70                  75                  80

Cys Gln Ser Gly Val Leu Glu Asp Gly Lys Cys Arg Thr Arg Ala Ala
                85                  90                  95

Glu Ala Phe Arg Cys Pro Asp Gly Phe Glu Thr Ile Cys Asp Ala Asn
            100                 105                 110

Ser Thr Ala Lys Ser Lys Cys Cys Arg Arg Thr Glu Ser Gln Glu Ile
        115                 120                 125

Asn Phe Lys Cys Ala Glu Gly Thr Thr Glu Thr Ile Asp Gly Asp Cys
    130                 135                 140

Lys Arg Leu Lys Gln Phe Pro Pro Ser His Glu Cys Pro Leu Gly Tyr
145                 150                 155                 160

Arg Tyr Asp Glu Arg Tyr Cys Val Arg Thr Glu Pro Gly His Val Val
                165                 170                 175

Pro Ala Cys Gly Val Glu Ser Gln Leu Thr Ala His Asn Ser Cys Leu
            180                 185                 190

Ser Ile Ala Pro Gly Glu Ile Val Tyr Glu Cys Pro Val Gly Phe His
        195                 200                 205
```

```
Cys Ala Ser Asn Ala Lys Asn Ser Asp Phe Cys Lys Ser Cys Lys Arg
        210                 215                 220

Arg Glu Leu Glu Pro Val Ser Cys Glu Cys Asp Ala Gly Thr Val Glu
225                 230                 235                 240

Ser Asp Gly Leu Cys Tyr Gln Ala Glu Glu Tyr His Glu Cys Phe Asp
                245                 250                 255

Lys Ile Lys Lys Asn Val Val Pro Thr Glu Val Val Asp Lys Asp Glu
            260                 265                 270

Asp Glu Lys Leu Asp Lys Lys Asp Lys Lys Cys Glu Thr Thr Arg
        275                 280                 285

Ser Lys Cys Ser Cys Arg Ala Gly Phe Asn Leu Val Cys Lys Gly Lys
        290                 295                 300

Glu Cys His Cys Val Lys Glu Glu Ser Ala Ala Val Val Arg Arg Cys
305                 310                 315                 320

Leu Gly Phe Asp Asp Gly Ser Gly Asn Cys Val Arg His Leu Glu Thr
                325                 330                 335

Ala Pro Val Tyr Gln Cys Gly Glu Gly Gln Glu Cys Glu Ile Val Gly
            340                 345                 350

Lys Lys Glu Cys Lys Cys Val Tyr Lys Ile Arg Lys Asp Ser Thr Ile
        355                 360                 365

Asn Cys Gly Asp Gly Val Leu Ile Gly Ser Asp Cys Phe Ser Val Glu
370                 375                 380

His Ile Pro Lys Thr Arg His Cys Gln Asp Gly Phe Asp Val Ala Cys
385                 390                 395                 400

Arg Arg Ser Glu Cys Gln Cys Glu Arg Asn Val Phe Thr Arg Arg Val
                405                 410                 415

Leu Thr Cys Asp Ala Glu Ala Lys Lys Ser Glu Gly Cys Ala Ser
            420                 425                 430

Leu Ser Glu Pro Glu Phe Ile Cys Lys Glu Gly Gln Leu Ile Asn Gly
        435                 440                 445

Asn Cys Val Arg Leu Ser Tyr Thr Val Glu Leu Cys Glu Ala
450                 455                 460
```

<210> SEQ ID NO 2
<211> LENGTH: 1389
<212> TYPE: DNA
<213> ORGANISM: Toxoplasma gondii

<400> SEQUENCE: 2

| | | | | | |
|---|---|---|---|---|---|
| atgccgacta | tctgttcaaa | gatcatttgt | gcgttgtctg | ttttgcttgc | aacaacagcc | 60 |
| cacgttccgg | gaatgcctgc | tttggcatcg | accgatgcca | ctatcatgaa | gaaggctccg | 120 |
| ggtacctatc | cagcacctcc | accagatcca | acaagagcca | ggtgcaagtg | cccgttcggc | 180 |
| tttgagaaaa | tggacaaatc | atgtgtgaag | aaggaggctg | caggacagcc | agaggctatc | 240 |
| tgccaatctg | tgttctgga | ggacggaaaa | tgcagaaccc | gggctgctga | agcctttcgc | 300 |
| tgtcctgacg | gctttgagac | tatctgtgac | gcaaactcta | cagcgaagtc | gaagtgctgc | 360 |
| cgccgaacag | agtcacaaga | aatcaatttt | aaatgtgccg | aaggaacaac | ggagactatt | 420 |
| gacggtgact | gcaagcgctt | gaagcagttt | ccgccaagtc | atgagtgtcc | cttgggctat | 480 |
| cggtacgatg | aaaggtactg | cgtcaggaca | gagcccggac | acgttgtgcc | tgcatgtggc | 540 |
| gtggagagtc | agttaacggc | gcacaactct | tgcctctcga | ttccccctgg | cgagatcgtg | 600 |
| tatgagtgcc | ctgtagggtt | tcattgtgcc | tcgaatgcga | agaactccga | cttttgcaaa | 660 |

| | |
|---|---|
| agctgcaaga ggagagagtt ggagcctgtc agttgtgagt gtgacgccgg caccgtagaa | 720 |
| agtgatggcc tctgctacca ggccgaagag taccatgagt gttttgacaa gataaagaaa | 780 |
| aatgtggtac ctaccgaggt cgtcgacaag gacgaagatg agaaattaga caagaaaaag | 840 |
| gacaagaagt gtgaaacaac aaggtcgaaa tgctcatgcc gcgctggctt caatctcgtg | 900 |
| tgcaagggaa aggagtgtca ctgtgtgaag gaagaatcgg ctgcagttgt aaggcgttgc | 960 |
| ctcgggtttg acgatggttc cggcaactgt gtgcgccact ggagacggc tcccgtttac | 1020 |
| caatgcggcg aaggacagga atgcgaaatc gtggggaaaa aagagtgcaa atgtgtctac | 1080 |
| aagatccgaa aagactctac gataaattgc ggcgacggcg tcctgatagg gagcgactgc | 1140 |
| ttttcggtgg agcacattcc gaaaacacga cattgtcagg atggcttcga tgttgcctgt | 1200 |
| cgcagatcgg aatgtcaatg cgaacgaaat gttttcacac gcagagtgct gacgtgtgat | 1260 |
| gctgaggcgg ccaaaaaatc tgaaggctgt gcaagtttat cagagccgga attcatctgc | 1320 |
| aaagagggtc aattgatcaa cggaaattgc gttagactgt catacacagt tgagttgtgc | 1380 |
| gaagcgtga | 1389 |

<210> SEQ ID NO 3
<211> LENGTH: 2357
<212> TYPE: DNA
<213> ORGANISM: Toxoplasma gondii

<400> SEQUENCE: 3

| | |
|---|---|
| accacacctt aacattctag aatctgaatt tgtttgtcac aacatcgcta ctttagtaat | 60 |
| cgcacatcgt aacgatgccg actatctgtt caaagatcat ttgtgcgttg tctgttttgc | 120 |
| ttgcaacaac agcccacgtt ccgggaatgc ctgctttggc atcgaccgat gccactatca | 180 |
| tgaagaaggc tccgggtacc tatccagcac ctccaccaga tccaacaaga gccaggtgca | 240 |
| agtgcccgtt cggctttgag aaaatggaca atcatgtgt gaagaaggag gctgcaggac | 300 |
| agccagaggt aaaacgggta ccgctcctca aaacagataa ttgctgatca acagttttac | 360 |
| aggctatctg ccaatctggt gttctggagg acggaaaatg cagaacccgg gctgctgaag | 420 |
| cctttcgctg tcctgacggc tttgagacta tctgtgacgc aaactctaca gcgaagtcga | 480 |
| agtgctgccg ccgaacagag tcacaagaaa tcaatttttaa atgtgccgaa ggaacaacgg | 540 |
| agactattga cggtgactgc aagcgcttga agcagtttcc gccaagtcat gagtgtccct | 600 |
| tgggctatcg gtacgatgaa aggtactgcg tcaggacaga gcccggacac gttgtgcctg | 660 |
| catgtggcgt ggagagtcag ttaacggcgc acaactcttg cctctcgatt gcccctggcg | 720 |
| agatcgtgta tgagtgccct gtagggttc attgtgcctc gaatgcgaag aactccgact | 780 |
| tttgcaaaag ctgcaagagg agagagttgg agcctgtcag ttgtgagtgt gacgccggca | 840 |
| ccgtagaaag tgatggcctc tgctaccagg ccgaagagta ccatgagtgt tttgacaaga | 900 |
| taaagaaaaa tgtggtacct accgaggtcg tcgacaagga cgaagatgag aaattagaca | 960 |
| agaaaaagga caagaagtgt gaaacaacaa ggtcgaaatg ctcatgccgc gctggcttca | 1020 |
| atctcgtgtg caagggaaag gagtgtcact gtgtgaagga agaatcggct gcagttgtaa | 1080 |
| ggcgttgcct cgggtttgac gatggttccg gcaactgtgt gcgccacttg agacggctc | 1140 |
| ccgtttacca atgcggcgaa ggacaggaat gcgaaatcgt ggggaaaaaa gagtgcaaat | 1200 |
| gtgtctacaa gatccgaaaa gactctacga taaattgcgg cgacggcgtc ctgatagga | 1260 |
| gcgactgctt tcggtggag cacattccga aaacacgaca ttgtcaggat ggcttcgatg | 1320 |
| ttgcctgtcg cagatcggaa tgtcaatgcg aacgaaatgt tttcacacgc agagtgctga | 1380 |

-continued

```
cgtgtgatgc tgaggcggcc aaaaaatctg aaggctgtgc aagtttatca gagccggaat    1440
tcatctgcaa agaggtaggc cggtcatcat tgtttataca aaacgcaaaa aaatgcttgc    1500
gttttttcag ggtcaattga tcaacggaaa ttgcgttaga ctgtcataca cagttgagtt    1560
gtgcgaagcg tgacctagtg tttcaaaatc aaattcggac actcctgtgc tggagcaaat    1620
gactttgttg ttgtatattg gtaccatata aaggactcgc gacacaccga tccatactgt    1680
aacatggtat ggacatcttg cattttcctc taggaaagag tgacaacacg agagagaaaa    1740
atagcgcttt caagctggca aactgccatt ccctttacct tggtatccgc ggagagaaag    1800
ccgcttcttc agcggtatct ttcaggtgtg gccaattggt caggaatatc tgagacattc    1860
cgttcaatta gaccagaccc agtctcatta gcgctgtgaa ttgccgcgga ttgaccccgt    1920
tccgtttacc cgttcggccg actcttgctg tactgcctta atggccgctc gctgcgactt    1980
cacacgttcc aaaacgtctg gctcgttcat gtctggccgc agaatccgat gcataacgca    2040
tgatccagcg aacgccgatg caaaagcgac gaacagagag agagcaaatt ctccacgggt    2100
gagacctgct ggcatcttgc cgaattaccg acgggttctt tccggttaag cctcacttgg    2160
tctttgctga gcaggctggt atgttgtcg gaagatatgg acacaacaga atagtaagag    2220
aacctggagc tagtgaaaca gaaatctgta aagcgtcccc aaaaccagca tgcctgaccg    2280
ggaaatggcc cctctagcac cgagacagca aggagcacgt taagcgtgat ctgattgtgg    2340
aatgtacaaa acatgtg                                                    2357
```

<210> SEQ ID NO 4
<211> LENGTH: 388
<212> TYPE: PRT
<213> ORGANISM: Toxoplasma gondii

<400> SEQUENCE: 4

```
Met Lys Ala Ala Val Ala Leu Ser Leu Phe Gly Leu Thr Leu Ala Leu
1               5                   10                  15

Pro Met Val Ala Leu Ala Glu Glu Met Ser Ser Glu Met Val Asp Ser
                20                  25                  30

Val Asp Met Leu Glu Met Glu Asp Val Ser Val Gln Glu Thr Gln Glu
            35                  40                  45

Leu Ser Glu Glu Ser Ser Thr Ala Pro Met Arg Tyr Leu Glu Glu Asp
        50                  55                  60

Ser Thr Asp Asp Ile Phe Leu Ile Pro Glu Thr Thr Ser Pro Ile Arg
65                  70                  75                  80

Val Leu Gly Lys Lys Asn Arg Ala Val Tyr Val Ala Ala Pro Lys Lys
                85                  90                  95

Tyr Val Ala Pro Val Val Gln Lys Lys Ala Pro Val Ala His Ser Lys
            100                 105                 110

Tyr Ser Ala Pro Ala Pro Ser Lys Lys Met His Ala Pro Ala Lys Lys
        115                 120                 125

Ala Pro Val Ile Met Ser Ser Lys Tyr Ala Pro Pro Ala Ser Lys
    130                 135                 140

Lys Tyr Thr Gln Ala Ala Pro Ser Lys Lys Tyr Arg Arg Leu Ala Pro
145                 150                 155                 160

Val Pro Glu Met Ser Glu Glu Ser Thr Ala Thr Ser Ile Ser Asp
                165                 170                 175

Ile Glu Val Asp Asp Glu Glu Arg Glu Leu Lys Lys Asn Ser Gly Tyr
            180                 185                 190
```

```
Tyr Val Ala Tyr Thr Pro Val Ala Ser Pro Tyr Cys Ser Val Gly
            195                 200                 205

Ser Ser Cys Ala Arg Tyr Leu Gly Glu Glu Gln Asp Met Asn Glu Glu
        210                 215                 220

Phe Met Ser Glu Glu Glu Ala Val Tyr Glu Gln Ser Ala Glu Glu
225                 230                 235                 240

Arg Ser Leu Gly Lys Lys Ser Arg Ala Val Tyr Ala Pro Ala Pro
                245                 250                 255

Lys Lys Tyr Val Ala Pro Ala Pro Gln Lys Lys Val Ala Ala Pro Val
            260                 265                 270

Tyr Arg Ala Ala Ser Met His Lys Lys Ala Glu Pro Val Val Gln Met
        275                 280                 285

Lys Ala Thr Pro Val Gln Lys Lys Ala Ala Pro Val Ala His Lys Lys
        290                 295                 300

Thr Pro Ala Phe Pro Ser Lys Lys Tyr His Gln Ala Met Ser Ser Ser
305                 310                 315                 320

Lys Tyr Thr Pro Ile Thr Thr Leu Ser Lys Lys Arg Arg Leu Ala Ala
                325                 330                 335

Gln Glu Asp Val Ala Val Glu Glu Glu Ser Thr Ala Thr Glu Thr Glu
            340                 345                 350

Thr Glu Glu Glu Glu Arg Asp Leu Lys Lys Arg Gly Thr Tyr Tyr Tyr
        355                 360                 365

Pro Val Ala Ala Tyr Pro Val Val Ala Thr Pro Tyr Cys Ser Thr Gly
        370                 375                 380

Gly Ala Cys Tyr
385

<210> SEQ ID NO 5
<211> LENGTH: 1167
<212> TYPE: DNA
<213> ORGANISM: Toxoplasma gondii

<400> SEQUENCE: 5
atgaaggcag ccgttgctct atctcttttc gggcttactc tggctctccc aatggtagct        60
ctggcagagg aaatgagcag cgaaatggtt gacagtgttg atatgctcga gatggaggat       120
gtttccgttc aggagaccca ggaactgtca gaggaatcta gcaccgcgcc catgcgttat       180
cttgaagaag atagcaccga cgacattttc ctcattcctg agaccactc tcccatccgc        240
gttctgggca agaaaaaccg tgccgtttac gtcgctgccc ccaagaagta tgtggctcct       300
gttgtgcaga agaaggcccc agttgcccac tccaagtact cggcacccgc ccgtccaag        360
aaaatgcacg cgcctgccaa gaaggcccca gttattatgt cgtccaagta cgcgcctgcc       420
cccgcctcga aaagtacac gcaagctgcc ccgtcgaaga agtatcgccg acttgcgccc       480
gttcccgaga tgtccgaaga ggaatcgact gcaacttcca tctcggacat cgaagtcgat       540
gatgaagaac gtgagctgaa gagaacagt ggctactatg ggcgtacac cccggtcgtt        600
gctagcccgt actgcagtgt cggctcatct tgtgctcgct acctcggtga agagcaagat       660
atgaacgagg agttcatgag cgaggaagag gaggctgtgt atgagcagag tgctgaagag       720
cgctccttgg gaagaagag ccgtgcggtt tacgtggccc ctgccccaaa aaagtacgtg        780
gcccccgctc ctcaaaagaa ggtcgctgct ccggtgtacc gtgcagcctc tatgcataag       840
aaggctgagc cggttgttca gatgaaggcc acgcctgttc agaagaaggc cgcgcctgtt       900
gctcataaga gacccccgc tttcccgtcg aagaaatacc atcaggctat gtcgtcatcc       960
```

```
aaatacactc ctatcactac tcttagcaag aagcgccgcc tggcagctca ggaagatgtt    1020
gctgtcgagg aggagtccac tgcgactgaa actgagacag aggaagagga gcgtgacctg    1080
aaaaaacgtg aacatacta ctacccggtt gctgcctacc cggtcgtcgc caccccgtac     1140
tgcagcaccg gtggtgcgtg ctactaa                                        1167
```

<210> SEQ ID NO 6
<211> LENGTH: 236
<212> TYPE: PRT
<213> ORGANISM: Toxoplasma gondii

<400> SEQUENCE: 6

```
Met Lys Gly Phe Ile Lys Ile Leu Leu Leu Gly Leu Leu Ala Val
1               5                   10                  15

Thr Thr Arg Thr Val Ala Gln Glu Thr Glu Glu Ala Lys Leu Thr Ser
            20                  25                  30

Asp Ser Glu Lys Val Ala Ala Ser Ser Asn Leu Thr Pro Asp Asn Ala
        35                  40                  45

Leu Ala Gly Ala Pro Gln Asn Glu Val Ala Ala Thr Glu Lys Val Thr
    50                  55                  60

Asp Glu Lys Gly Ser Gly Glu Glu Ala Ala Glu Pro Asp Glu Asp Lys
65                  70                  75                  80

Lys Asp Asp Gly Glu Ala Thr Asn Asn Glu Asp Glu Gln Lys Gly Asp
                85                  90                  95

Asp Asp Ala Lys Asp His Ala Asp Glu Gln Lys Asp Lys Lys Gln
            100                 105                 110

Gly Asn Asp Glu His Ser Ser Gln Lys Leu Ser Phe Ile Glu Cys Asp
        115                 120                 125

Cys Arg Lys Lys Arg Val Arg Gly Thr Gly Ala Pro Cys Ser Cys Ala
    130                 135                 140

Asp Leu Val Lys Glu Ala Phe Arg His Ser Leu Leu Pro Trp Phe Leu
145                 150                 155                 160

Pro Gly Phe Phe Pro Arg Gln Glu Ser Glu Gly Ser Thr Met Lys Pro
                165                 170                 175

Arg Leu Ser Gly Arg Gln Arg Leu Leu Gly Leu Gly Asn Leu Phe Gly
            180                 185                 190

Gly Tyr Tyr Pro Gly Tyr Gly Tyr Gly Tyr Pro Gly Tyr Gly Tyr Gly
        195                 200                 205

Tyr Gly Tyr Gly Tyr Pro Gly Tyr Gly Tyr Pro Gly Tyr Gly Phe Gly
    210                 215                 220

Gly Phe Gly Pro Gly Phe Gly Val Gly Phe Thr Phe
225                 230                 235
```

<210> SEQ ID NO 7
<211> LENGTH: 711
<212> TYPE: DNA
<213> ORGANISM: Toxoplasma gondii

<400> SEQUENCE: 7

```
atgaaaggct tcatcaagat tcttctgctc cttggcctcc tggccgtgac aaccaggacc     60
gtcgctcaag agactgagga ggcgaagttg acgagtgact ccgaaaaggt tgccgcgtcc    120
agcaacctca ctcctgataa tgcgctcgct ggcgctccac agaatgaggt ggctgccaca    180
gaaaaggtga cagacgagaa aggcagcggt gaagaggctg cggaacccga cgaggacaag    240
aaagacgatg gcgaggcaac gaacaatgag gacgaacaga aggcgatgga cgatgcaaag    300
```

| | |
|---|---|
| gatcacgctg atgaacagaa agacgataag aagcaaggta atgatgaaca ctcctcccag | 360 |
| aaactctcgt ttatcgaatg cgactgcaga aaaaagcgcg ttcgcggcac cggcgctccc | 420 |
| tgttcttgtg ctgaccttgt gaaagaagcg ttccgccaca gcctgctgcc ttggtttctc | 480 |
| cctggattct ttccgagaca agagtcggaa ggtagtacga tgaaaccgcg cctctcgggc | 540 |
| cgtcaacggc ttctgggact cggcaatctt ttcggtggat actatcccgg ctacggctac | 600 |
| ggatatcctg gatatggcta cggatatggc tatggctatc ccggctacgg ctatcctgga | 660 |
| tacggcttcg gaggcttcgg tcctggtttt ggtgttggct tcacattcta a | 711 |

<210> SEQ ID NO 8
<211> LENGTH: 222
<212> TYPE: PRT
<213> ORGANISM: Toxoplasma gondii

<400> SEQUENCE: 8

Met Thr Arg Ser Arg Val Leu Cys Ser Val Ala Leu Leu Ala Ser Thr
1               5                   10                  15

Gln Leu Leu Ser Trp Ala Gln Ala Asp Asp Pro Val Val Ser Val Glu
            20                  25                  30

Glu Leu Ile Arg Ser Glu Glu Pro Gly Thr Ile Ser Ala Ser Ser Ala
        35                  40                  45

Gly Asp Tyr Gly Leu Ile Glu Asp Pro Glu Asp Thr Arg Glu Met Ser
    50                  55                  60

His His Arg Arg Tyr Ser Tyr Pro Ala Ser Tyr Val Leu Pro Ser Pro
65                  70                  75                  80

Val Tyr Tyr Pro Arg Ser His Tyr Pro Arg Tyr Leu Val Asn Gln
                85                  90                  95

Lys Ala Phe Lys Glu Asp Asp Met Gln Thr Val Asp Asp Gln Glu Glu
            100                 105                 110

Met Ser Pro Val Ala Pro Pro Ala Gly Glu Arg Asp Leu Ser His Arg
        115                 120                 125

Arg His His Ser Pro Ala Pro Tyr Gly Tyr Tyr Ser Pro Ala Glu
    130                 135                 140

Tyr Tyr Thr Pro Lys His Tyr Val Gly Ser Pro Tyr Pro Arg Tyr Leu
145                 150                 155                 160

Lys Glu Ala Arg Arg Ala Ala Val Val Asp Lys Ser Ala Ala Ala Gln
                165                 170                 175

Ser Lys Phe Met Ala Ala Ser Arg Lys Val Arg Asn Met Gly His Arg
            180                 185                 190

Arg Tyr Gly Tyr Tyr His Val Pro Leu Pro Tyr Tyr Ser Ser Tyr Tyr
        195                 200                 205

Gly Tyr Arg Asn Ser Pro Tyr Gly Tyr Val Arg Tyr Leu Tyr
    210                 215                 220

<210> SEQ ID NO 9
<211> LENGTH: 669
<212> TYPE: DNA
<213> ORGANISM: Toxoplasma gondii

<400> SEQUENCE: 9

| | |
|---|---|
| atgacaaggt cacgtgtgct gtgcagcgta gcgctattgg cgtctacgca attgctgtcc | 60 |
| tgggcccaag ctgatgatcc ggtcgtgtcc gtcgaggagc tcatccggtc ggaagaacca | 120 |
| ggcacaattt ccgcaagcag tgcgggagac tatggcctta gaggacccc agaagataca | 180 |
| agggagatgt ctcatcaccg gaggtactcc taccccgcca gttacgtact tccctcaccg | 240 |

```
gtgtattatc cccgttctca ctactatccc aggtatcttg tgaaccagaa ggctttcaaa      300
gaagatgaca tgcagactgt ggatgaccag gaggaaatga gtcctgttgc gcctcctgca      360
ggggagcgag atttgtctca ccgtcgccac cacagtcccg ccccgtacgg ctattattac      420
tcccccgcag aatactatac cccaaagcac tacgtgggaa gtccttatcc cagatatctc      480
aaagaggcac ggcgtgcggc agttgtcgat aaaagtgcag cggcgcagtc gaagttcatg      540
gctgcatcta ggaaagttag gaacatggga catcgccggt atggctacta ccacgtcccc      600
cttccttact acagctctta ctacggatac aggaactcgc cttacggtta tgtccgctat      660
ctctattga                                                              669
```

<210> SEQ ID NO 10
<211> LENGTH: 113
<212> TYPE: PRT
<213> ORGANISM: Toxoplasma gondii

<400> SEQUENCE: 10

Met Tyr Phe Lys Met Lys Val Phe Asn Phe Val Leu Leu Met Ala Ile
1               5                   10                  15

Ile Ala Ala Ser Val Ser Ala Ala Lys Ala Glu Ser Glu His Val Gly
            20                  25                  30

Asp Ala Lys Pro Leu His Lys Glu Ile Arg Ala Glu Gln Pro Ser Val
        35                  40                  45

Val Gln Glu Gly Leu Gln Gln Asn Arg Asp Asn Pro Thr Arg Glu Leu
    50                  55                  60

Phe Pro Arg Leu Trp Gly Tyr Gly Gly Tyr Tyr Gly Tyr Pro Tyr
65                  70                  75                  80

Ala Gly Tyr Ser Tyr Gly Tyr Gly Tyr Pro Tyr Ala Gly Tyr Thr
                85                  90                  95

Tyr Tyr Gly Tyr Pro Tyr Gly Ala Tyr Tyr Gly Tyr Gly Tyr Tyr
            100                 105                 110

Trp

<210> SEQ ID NO 11
<211> LENGTH: 342
<212> TYPE: DNA
<213> ORGANISM: Toxoplasma gondii

<400> SEQUENCE: 11

```
atgtatttta agatgaaggt gttcaacttc gttttgctca tggccatcat tgccgcgtct      60
gtgtcggctg ccaaagcgga atccgaacat gttggtgacg cgaagcccttgcacaaagaa      120 atccgcgccg aacagccatc ggttgtgcag gaaggacttc aacagaacag agataatcct      180
acacgggagc tattccccag actctggggg tatggaggct acggttacgg ctacccctac      240
gcagggtaca gctacggcta ctacggctac ccatatgcag gatacaccta ctacggctac      300
ccgtatggtg catactatgg ctacggtggg tattactggt aa                         342
```

<210> SEQ ID NO 12
<211> LENGTH: 998
<212> TYPE: DNA
<213> ORGANISM: Toxoplasma gondii

<400> SEQUENCE: 12

```
ataaatcata taatcacgtc cgtcacactt caatttgtta cttcacgttc tgctcttccg      60
acagtctacg ttaggtgcaa cgacttcgtc taattccaac atccaggaac accaacgttc      120
```

```
tatgtatttt aagatgaagg tgttcaactt cgttttgctc atggccatca ttgccgcgtc    180
tgtgtcggct gccaaagcgg aatccgtaag cattaacgta attggtcacc tgcagggcaa    240
gcgtcttcca ggaaatcgcc tttgatatgc ccgtcacacg tgtgtgtgat ttttcaggaa    300
catgttggtg acgcgaagcc cttgcacaaa gaaatccgcg ccgaacagcc atcggttgtg    360
caggaaggac ttcaacagaa cagagataat cctacacggg agctattccc cagactctgg    420
gggtatggag gctacggtta cggctacccc tacgcagggt acagctacgg ctactacggc    480
tacccatatg caggatacac ctactacggc tacccgtatg gtgcatacta tggctacggt    540
gggtattact ggtaactgtg cgaacaaaaa ttacagtcac gatcaaatct gttgtcatgc    600
ctggaaccac agatacccctg ttggagcagg cagctactga tgcagatttc cagagtatgg    660
cttctgagag gatgacgatg gggatggaat tagctgaggg atcaggggaa aagtgctcca    720
agttcgtgtg gccgcgccaa ccgatgggaa tttttaacga cgaatatgtg gttccatgtt    780
cgggtataat ttgaacccgg ttcacgaaga aacgtttttc taatctaaag ttgttgtcgc    840
agtaaacgac gtgtagggtc tccgctgaat tgactggcac tctgcttggt caagagcccc    900
tgtctagcct atacacagct aggaacgaac gtttgacatg cgcttcatca accaaacatg    960
tagactatcg cacagttaaa gggcagtgct ttaaaaaa                            998
```

<210> SEQ ID NO 13
<211> LENGTH: 574
<212> TYPE: PRT
<213> ORGANISM: Toxoplasma gondii

<400> SEQUENCE: 13

```
Met Lys Leu Leu Thr Pro Leu Phe Leu Ser Gly Leu Val Val Ala Ala
 1               5                  10                  15

Ala Ala Gln Asp Gly Gln Glu Pro Ser Glu Leu Ala Glu Gln Ile
            20                  25                  30

Val Ser Ser Leu Gly Pro Asp Asp Val Glu Asp Gly Ala Asp Asp Arg
 35                  40                  45

Glu Leu Gly Gly Lys Lys Ser Gly Gly Tyr Ile Pro Ala Met Pro Val
 50                  55                  60

Lys Lys Thr Pro Val Thr Lys Val Thr Tyr Leu Pro Thr Pro Lys Lys
 65                  70                  75                  80

Ala Ala Gln Pro Ile Val Tyr Ala Ser Ser Lys Lys Gly Asp Tyr Leu
                85                  90                  95

Pro Arg Lys Leu Gln Asp Ile Asp Thr Asp Glu Thr Asp Ala Ile Arg
            100                 105                 110

Ser Asp Glu Glu Leu Asp Thr Glu Ser Gln Thr Ala Asp Glu Ser
            115                 120                 125

Ala Asp Asp Arg Glu Leu Gly Gly Lys Lys Asn Arg Gly Gly Tyr Ile
            130                 135                 140

Pro Val Lys Leu Pro Pro Lys Lys Val Val Ala Pro Lys Lys
145                 150                 155                 160

Val Ala Thr Pro Ile Tyr Ala Gly Lys Lys Gly Tyr Trp Gly Gly Gly
                165                 170                 175

Tyr Tyr Arg Arg Leu Gly Glu Glu Pro Asp Thr Glu Asp Glu Leu Val
            180                 185                 190

Glu Glu Leu Glu Ala Glu Glu Pro Glu Glu Ser Gln Thr Ala Asp Glu
        195                 200                 205

Ser Ala Asp Asp Arg Glu Leu Gly Gly Lys Lys Asn Arg Gly Gly Tyr
```

```
        210                 215                 220
Ile Pro Val Lys Leu Pro Pro Lys Val Val Ala Pro Lys
225                 230                 235                 240

Lys Val Ala Thr Pro Ile Tyr Ala Gly Lys Lys Gly Tyr Trp Gly Gly
                245                 250                 255

Gly Tyr Tyr Arg Arg Leu Gly Glu Glu Pro Asp Thr Glu Asp Glu Leu
                260                 265                 270

Val Glu Glu Leu Glu Ala Glu Glu Pro Glu Glu Ser Gln Thr Ala Asp
            275                 280                 285

Glu Ser Ala Asp Asp Arg Glu Leu Gly Gly Lys Lys Asn Arg Gly Gly
        290                 295                 300

Tyr Ile Pro Val Lys Leu Pro Pro Lys Lys Val Val Ala Pro
305                 310                 315                 320

Lys Lys Val Ala Thr Pro Ile Tyr Ala Gly Lys Lys Gly Tyr Trp Gly
                325                 330                 335

Gly Gly Tyr Tyr Arg Arg Leu Gly Glu Glu Pro Asp Thr Glu Asp Glu
                340                 345                 350

Leu Val Val Glu Leu Glu Ala Glu Glu Pro Glu Glu Ser Gln Thr Ala
            355                 360                 365

Asp Glu Ser Ala Asp Asp Arg Glu Leu Gly Gly Lys Lys Asn Arg Gly
        370                 375                 380

Gly Tyr Ile Pro Val Lys Leu Pro Pro Lys Lys Val Val Ala
385                 390                 395                 400

Pro Lys Lys Val Ala Thr Pro Ile Tyr Ala Gly Lys Lys Gly Tyr Trp
                405                 410                 415

Gly Gly Gly Tyr Tyr Arg Arg Leu Gly Glu Glu Pro Asp Thr Glu Asp
                420                 425                 430

Glu Leu Val Glu Glu Leu Glu Ala Glu Glu Pro Glu Glu Leu Gln Ala
            435                 440                 445

Gln Glu Pro Glu Glu Ser Ala Asp Glu Ala Ala Asp Gly Arg Glu Leu
        450                 455                 460

Gly Lys Ser Thr Tyr Gly Gly Tyr Ser Tyr Ser Pro Ser Ser Lys Lys
465                 470                 475                 480

Thr Thr Val Gln Pro Ser Tyr Thr Thr Lys Val Val Arg Arg Pro Lys
                485                 490                 495

Lys Val Asp Gln Pro Ala Pro Lys Lys Leu Ile Arg Ser Glu Pro Lys
                500                 505                 510

Lys Ser Val Ser Tyr Gln Pro Lys Lys Thr Val Arg Thr Val Ser Lys
            515                 520                 525

Lys Thr Val Ser Pro Val Pro Lys Lys Ala Val Gln Ala Gln Pro Lys
        530                 535                 540

Lys Thr Leu Ser Tyr Arg Pro Val Ile Glu Ala Gln Thr Lys Lys Ser
545                 550                 555                 560

Thr His Tyr Ala Pro His Tyr Thr Ser Lys Lys Gly Ser Tyr
                565                 570

<210> SEQ ID NO 14
<211> LENGTH: 1725
<212> TYPE: DNA
<213> ORGANISM: Toxoplasma gondii

<400> SEQUENCE: 14
atgaagctct tgactcccct ttttctgtcc gggcttgttg tggcagcggc agctcaagac      60
ggacaagagc ctcccagtga gttagcggaa cagatcgttt cttctcttgg cccggacgat     120
```

```
gtagaggatg cgcctgacga tcgagagctc ggaggtaaaa aatcgggtgg ctatattcct        180
gctatgccag tgaagaagac accagtaacc aaagtgacct atttgcccac tccgaagaaa        240
gcagcccagc caattgtcta cgcatcatcc aaaaaaggtg actacctacc acgcaagctc        300
caagacatcg atacagacga gactgatgcc atccgctccg acgaagaact cgacacagag        360
gaatcacaga cggccgacga atcggccgat gatcgcgaac tcggggggcaa gaagaatcgt       420 ggtggctata ttcctgtaaa gctaccaccg cccaaaaaag ttgtcgttgc tcccaagaag        480
gtggccactc cgatctacgc tggcaagaaa ggatactggg gcggaggcta ctaccgccgc        540
ctcggtgagg aaccagatac agaagacgag ctcgtcgagg aactggaggc cgaagagccc       600
gaggaatcac agacggccga cgaatcggcc gatgatcgcg aactcggggg caagaagaat       660
cgtggtggct atattcccgt aaagctacca ccgcccaaaa aagttgtcgt tgctcccaag       720
aaggtggcca ctccgatcta cgctggcaag aaaggatact ggggcggagg ctactaccgc       780
cgcctcggtg aggaaccaga tacagaagac gagctcgtcg aggaactgga ggccgaagag       840
cccgaggaat cacagacggc cgacgaatcg gccgatgatc gcgaactcgg ggcaagaag       900 aatcgtggtg gctatattcc tgtaaagcta ccaccgccca aaaagttgt cgttgctccc       960 aagaaggtgg ccactccgat ctacgctggc aagaaaggat actggggcgg aggctactac      1020
cgccgcctcg gtgaggaacc agatacagaa gacgagctcg tcgttgaact ggaggccgaa      1080
gagcccgagg aatcacagac ggccgacgaa tcggccgatg atcgcgaact cggggggcaag     1140 aagaatcgtg gtggctatat tcctgtaaag ctaccaccgc ccaaaaaagt tgtcgttgct      1200
cccaagaagg tggccactcc gatctacgct ggcaagaaag gatactgggg cggaggctac      1260
taccgccgcc tcggtgagga accagataca gaagacgagc tcgtcgagga actggaggcc      1320
gaagagcccg aggaattaca ggcacaagag cccgaggagt cggcagatga ggctgccgac      1380
ggccgcgaac tcggcaaaag cacgtacggt ggctacagct actctccgtc agcaaaaaag      1440
acaaccgtac agccttccta caccactaaa gttgttcgac gccccaaaaa ggttgaccag      1500
cctgcgccaa agaagctcat cgctccgag cccaagaaaa gcgttagcta tcagccgaag       1560
aagactgtac gtacagtctc taagaaaact gtgagtccgg ttccgaaaaa ggctgttcag      1620
gcgcagccga agaagaccct cagttaccga ccggtaattg aggcgcaaac aaagaagagc      1680
acgcactacg ctcctcatta tacttcaaag aagggatcgt actaa                      1725
```

<210> SEQ ID NO 15
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 15
atgccgacta tctgttcaaa gatcatttgt gc                                       32

<210> SEQ ID NO 16
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 16
cctccagaac accagattgg cagatagcct ctggctgtcc tgcagcctcc ttc                53

<210> SEQ ID NO 17
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 17
gaaggaggct gcaggacagc cagaggctat ctgccaatct ggtgttctgg agg    53

<210> SEQ ID NO 18
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 18
gtctaacgca atttccgttg atcaattgac cctctttgca gatgaattcc ggctctgata    60
aa    62

<210> SEQ ID NO 19
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 19
tttatcagag ccggaattca tctgcaaaga gggtcaattg atcaacggaa attgcgttag    60
ac    62

<210> SEQ ID NO 20
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 20
cgcttcgcac aactcaactg tgtatgaca    29

<210> SEQ ID NO 21
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 21
ccagaacgag gctgccaact gtact    25

<210> SEQ ID NO 22
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 22
ctgcaagtag gtcttaatgg aaagaagtat gg    32

<210> SEQ ID NO 23
<211> LENGTH: 57

```
<212> TYPE: DNA
<213> ORGANISM: Artificial Sequence
<220> FEATURE:
<223> OTHER INFORMATION: synthetic oligonucleotide

<400> SEQUENCE: 23
cctgatgttc atcgctttcg tcatcatcgc tgaggcccac gttccgggaa tgcctgc      57

<210> SEQ ID NO 24
<211> LENGTH: 78
<212> TYPE: DNA
<213> ORGANISM: Artificial Sequence
<220> FEATURE:
<223> OTHER INFORMATION: synthetic oligonucleotide

<400> SEQUENCE: 24
agtcatcgac actagtttaa tggtggtgat ggtgatgtcc acctgaacct cccgcttcgc   60
acaactcaac tgtgtatg                                                 78

<210> SEQ ID NO 25
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 25
ctgataagtt acggaccgag ccgccaccat gtacaagctc acagtcttcc tgatgttcat   60
cgctttcgtc atc                                                      73

<210> SEQ ID NO 26
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 26
cctgatgttc atcgctttcg tcatcatcgc tgaggccgag gaaatgagca gcgaaatggt   60
tg                                                                  62

<210> SEQ ID NO 27
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 27
agtcatcgac actagtttaa tggtggtgat ggtgatgtcc acctgaacct ccgtagcacg   60
caccaccggt gct                                                      73

<210> SEQ ID NO 28
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 28
ctgataagtt acggaccgag ccgccaccat gtacaagctc acagtcttcc tgatgttcat   60
cgctttcgtc atc                                                      73
```